US012411750B2

(12) United States Patent
Sun et al.

(10) Patent No.: US 12,411,750 B2
(45) Date of Patent: Sep. 9, 2025

(54) COGNITIVE BIAS DETECTION AND CORRECTION IN SELF-REPORTED DATA

(71) Applicant: International Business Machines Corporation, Armonk, NY (US)

(72) Inventors: Si Sun, Whitestone, NY (US); Zhiguo Li, Yorktown Heights, NY (US); Chandramouli Maduri, Elmsford, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1017 days.

(21) Appl. No.: 17/488,125

(22) Filed: Sep. 28, 2021

(65) Prior Publication Data

US 2023/0101200 A1 Mar. 30, 2023

(51) Int. Cl.

| | |
|---|---|
| ***G06F 11/34*** | (2006.01) |
| ***A61B 5/00*** | (2006.01) |
| ***A61B 5/0205*** | (2006.01) |
| ***A61B 5/16*** | (2006.01) |
| ***G06F 16/36*** | (2019.01) |
| ***G06N 3/08*** | (2023.01) |

(Continued)

(52) U.S. Cl.
CPC .......... *G06F 11/3438* (2013.01); *A61B 5/165* (2013.01); *G06F 16/367* (2019.01); *G06N 20/00* (2019.01); *A61B 5/0205* (2013.01); *A61B 5/6898* (2013.01); *G06F 2201/86* (2013.01); *G06N 3/08* (2013.01); *G06N 5/01* (2023.01); *G06N 20/20* (2019.01)

(58) Field of Classification Search
CPC ............... G06F 11/3438; G06F 16/367; G06F 2201/86; A61B 5/165; A61B 5/7264; A61B 5/0205; A61B 5/6898; G06N 20/00; G06N 3/08; G06N 5/01; G06N 20/10; G06N 20/20
See application file for complete search history.

(56) References Cited

U.S. PATENT DOCUMENTS

| | | | |
|---|---|---|---|
| 10,572,679 | B2 | 2/2020 | Frank et al. |
| 2012/0259240 | A1 | 10/2012 | Llewellynn et al. |

(Continued)

FOREIGN PATENT DOCUMENTS

| | | |
|---|---|---|
| CN | 107169272 | 9/2017 |

OTHER PUBLICATIONS

Golemati et al., NPL1 ("Creating an Ontology for the User Profile: Method and Applications" Published Oct. 21, 2006—total 6 pages ( Year: 2006).*

(Continued)

*Primary Examiner* — Quoc A Tran
(74) *Attorney, Agent, or Firm* — Amin, Turocy & Watson, LLP

(57) ABSTRACT

Embodiments are provided for cognitive bias detection and correction in self-reported data. In some embodiments, a system can include a processor that executes computer-executable components stored in memory. The computer-executable components include first components that creates an ontology of bias descriptor features to identify cognitive biases. The cognitive biases can include a combination of at least one device-induced cognitive bias, at least one testing-application-induced cognitive bias, or at least one study-design-induced cognitive bias.

20 Claims, 15 Drawing Sheets

(51) Int. Cl.

| | |
|---|---|
| ***G06N 5/01*** | (2023.01) |
| ***G06N 20/00*** | (2019.01) |
| ***G06N 20/20*** | (2019.01) |

(56) References Cited

U.S. PATENT DOCUMENTS

| | | | | |
|---|---|---|---|---|
| 2015/0269139 | A1* | 9/2015 | McAteer | G06F 40/30 704/9 |
| 2015/0339584 | A1 | 11/2015 | Baughman et al. | |
| 2016/0086091 | A1 | 3/2016 | Ellis | |
| 2016/0260341 | A1 | 9/2016 | Baughman et al. | |
| 2017/0309193 | A1 | 10/2017 | Joseph et al. | |
| 2020/0327895 | A1* | 10/2020 | Gruber | G10L 17/22 |
| 2021/0117814 | A1* | 4/2021 | Flinn | G06N 5/045 |

OTHER PUBLICATIONS

Ismael et al., NPL2 ("A Survey on Bias in Deep NLP" Published 2021, 26 pages, (Year: 2021).*

Spitzer et al., "Reporting biases in self-assessed physical and cognitive health status of older Europeans," PloS one, 14(10), Oct. 8, 2019, 22 pages.

Dowling et al., "Measurement and control of bias in patient reported outcomes using multidimensional item response theory," BMC medical research methodology, 16(1), 63, 2016, 12 pages.

Peters et al., "Cognitive bias modification for facial interpretation: a randomized controlled trial of transfer to self-report and cognitive measures in a healthy sample," Royal Society open science, 4(12), 170681, 2017, 13 pages.

Liechty et al., "Feasibility and validity of a statistical adjustment to reduce self-report bias of height and weight in wave 1 of the Add Health study," BMC medical research methodology, 16(1), 124, 2016, 10 pages.

Roy et al., "Correcting Bias in Crowdsourced Data to Map Bicycle Ridership of All Bicyclists," Urban Science, 3(2), 62, 2019, 20 pages.

Festinger, "Cognitive dissonance," Scientific American, 207(4), 93-107, 1962, 14 pages.

Rosenman et al., "Measuring bias in self-reported data," Int J Behav Healthc Res. Oct. 2011 ; 2(4): 320-332, 15 pages.

Tennekoon et al., "Bias in Measuring Smoking Behavior," Washington State University—School of Economic Sciences, Working Paper Series, WP Oct. 2013, Aug. 2013, 21 pages.

Tennekoon et al., "Systematically Misclassified Binary Dependent Variables," Commun Stat Theory Methods. 2016 ; 45(9): 2538-2555, 26 pages.

Geisen et al., "Examining the relationship between the accuracy of self-reported data and the availability of respondent financial records, " https://www.rti.org/sites/default/files/resources/aapor12_geisen_paper.pdf, 2012, 9 pages.

Rader et al., "Bias-corrected estimates for logistic regression models for complex surveys with application to the United States' Nationwide Inpatient Sample," Stat Methods Med Res. Oct. 2017;26(5):2257-2269, 23 pages.

Mell et al., "The NIST Definition of Cloud Computing," Recommendations of the National Institute of Standards and Technology, NIST Special Publication 800-145, Sep. 2011, 7 pages.

* cited by examiner

SS ~ HRV1 + UI + ES + E + T + D +P
SS ~ HRV2 + UI + ES + E + T + D +P
SS ~ HRV3 + UI + ES + E + T + D +P
SS ~ HRV1 + E + T + D +P
SS ~ HRV2 + E + T + D +P
SS ~ HRV3 + E + T + D +P
SS ~ HRV1 + HRV2+ HRV3+ UI + ES + E + T + D +P
SS ~ HRV1 + HRV2+ HRV3 + ES + E + T + D +P
SS ~ HRV1 ~ HRV2 ~ HRV 3
HRV2 - HRV1 ~ UI + ES + E + T + D +P
HRV3 - HRV1 ~ UI + ES + E + T + D +P
HRV2 - HRV1 ~ E + T + D +P
HRV3 - HRV1 ~ E + T + D +P
HRV1 ~ SS + UI + ES + E + T + D +P
HRV2 ~ SS + UI + ES + E + T + D +P
HRV3 ~ SS + UI + ES + E + T + D +P
HRV1 ~ SS + E + T + D +P
HRV2 ~ SS + E + T + D +P

FIG. 4A

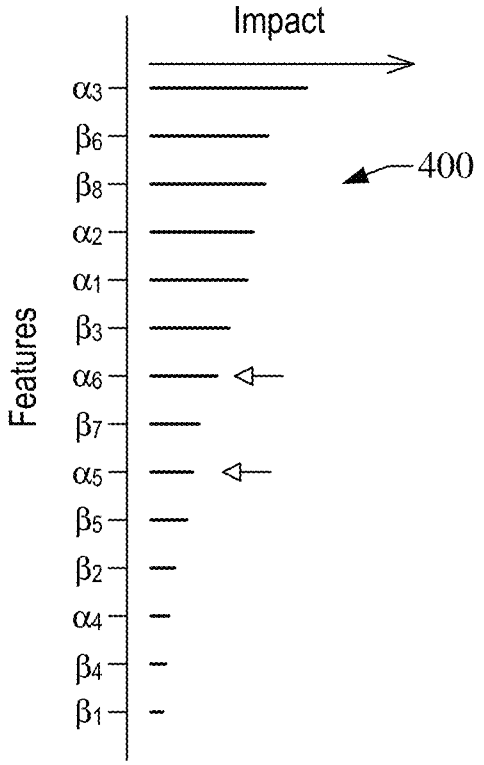

FIG. 4B 685 687

| Feature | Description |
|---|---|
| all_probe_freq_interact_cancel_notif_all | All probes(event, time and user probe) : Number of notifications are cancelled overall |
| all_probe_freq_interact_cancel_notif_day | All probes(event, time and user probe) : Number of notifications are cancelled |
| all_probe_freq_interact_cancel_notif_hr | All probes(event, time and user probe) : Number of notifications are cancelled per hour |
| all_probe_freq_interact_no_resp_notif_all | All probes(event, time and user probe) : Number of notifications are not responded overall |
| all_probe_freq_interact_no_resp_notif_day | All probes(event, time and user probe) : Number of notifications are not responded per day |
| all_probe_freq_interact_no_resp_notif_hr | All probes(event, time and user probe) : Number of notifications are not responded per hour |
| all_probe_freq_interact_ok_notif_all | All probes(event, time and user probe) : Number of notifications are responded/ok overall |
| all_probe_freq_interact_ok_notif_day | All probes(event, time and user probe) : Number of notifications are responded/ok per day |
| all_probe_freq_interact_ok_notif_hr | All probes(event, time and user probe) : Number of notifications are responded/ok per hour |
| all_probe_overall_freq_incomplete_notifications_day_subject | All probes(event, time and user probe) : Number of notifications are incompleted per day/subject |
| all_probe_overall_freq_incomplete_notifications_hr_day | All probes(event, time and user probe) : Number of notifications are incompleted per hr/day |
| all_probe_overall_freq_notifications_day_subject | All probes(event, time and user probe) : Number of notifications are received per day/subject |
| all_probe_overall_freq_notifications_hr_day | All probes(event, time and user probe) : Number of notifications are received per hr/day |
| all_probe_overall_freq_notifications_hr_subject | All probes(event, time and user probe) : Number of notifications are received per hr/subject |
| all_probe_total_freq_notif_all | All probes(event, time and user probe) : Number of notifications are received |
| all_probe_total_freq_notif_day | All probes(event, time and user probe) : Number of notifications are received per |
| all_probe_total_freq_notif_hr | All probes(event, time and user probe) : Number of notifications are received per |
| dwell_event_intro_log_time | Dwelling time on event logging intro page |
| dwell_event_log_screens | Dwelling screens on event logging page |
| dwell_event_log_time | Dwelling time on event logging page |
| dwell_stress_intro_log_time | Dwelling time on stress logging intro page |
| dwell_stress_log_screens | Dwelling screens on stress logging page |
| dwell_stress_log_time | Dwelling time on stress logging page |
| event_base_freq_interact_cancel_notif_all | Event-basedprobing : Number of notifications are cancelled overall |
| event_base_freq_interact_cancel_notif_day | Event-basedprobing : Number of notifications are cancelled per day |
| event_base_freq_interact_cancel_notif_hr | Event-basedprobing : Number of notifications are cancelled per hour |
| event_base_freq_interact_no_resp_notif_all | Event-basedprobing : Number of notifications are not responded overall |
| event_base_freq_interact_no_resp_notif_day | Event-basedprobing : Number of notifications are not responded per day |
| event_base_freq_interact_no_resp_notif_hr | Event-basedprobing : Number of notifications are not responded per hour |
| event_base_freq_interact_ok_notif_all | Event-basedprobing : Number of notifications are responded/ok overall |
| event_base_freq_interact_ok_notif_day | Event-basedprobing : Number of notifications are responded/ok per day |
| event_base_freq_interact_ok_notif_hr | Event-basedprobing : Number of notifications are responded/ok per hour |
| event_base_overall_freq_incomplete_notifications_day_subject | Event-basedprobing : Number of notifications are incompleted per day/subject |
| event_base_overall_freq_incomplete_notifications_hr_day | Event-basedprobing : Number of notifications are incompleted per hr/day |
| event_base_overall_freq_notifications_day_subject | Event-basedprobing : Number of notifications are received per day/subject |
| event_base_overall_freq_notifications_hr_day | Event-basedprobing : Number of notifications are received per hr/day |
| event_base_overall_freq_notifications_hr_subject | Event-basedprobing : Number of notifications are received per hr/subject |
| event_base_total_freq_notif_all | Event-basedprobing : Number of notifications are received overall |
| event_base_total_freq_notif_day | Event-basedprobing : Number of notifications are received per day |
| event_base_total_freq_notif_hr | Event-basedprobing : Number of notifications are received per hour |

| Feature | Description |
|---|---|
| is_familiar_with_events | Participants familiarity with event labeling (scrollthrough 1 direction Ðfamiliar; scroll both directions Ðunfamiliar; or a continuous variable of steps taken versus steps needed to get to the final entry) |
| openness__event_discrepancy | Discrepancy in perceived and objective openness to receiving more event base notification (calculate x = (proposed frequency of notifications Ðactual notification frequency (i.e., event-based probing)), values could be >0, =0, or <0; y = perceived frequency of notifications; normalize x and y; compare x and y) |
| openness_event | Objective openness to receiving more event based notifications (proposed frequency of event based notifications Ðactual event based notification frequency (i.e., event-based probing)) |
| openness_subject | Objective openness to receiving more notifications (proposed frequency of notifications Ðactual notification frequency (i.e., event-based + time-based |
| openness_subject_discrepancy | Discrepancy in perceived and objective openness to receiving more notification (calculate x = (proposed frequency of notifications Ðactual notification frequency (i.e., event-based + time-based probing)), values could be >0, =0, or <0; y = perceived frequency of notifications; normalize x and y; compare x and y) |
| prb_to_resp_time | Time difference between probe initiated and response time |
| probe_status | Probe status |
| probe_type | Type of probobing event-based/time-based/User initiated |
| proposed_best_frequency_notifications | Proposed best frequency notifications |
| time_base_freq_interact_cancel_notif_all | Time-basedprobing : Number of notifications are cancelled overall |
| time_base_freq_interact_cancel_notif_day | Time-basedprobing : Number of notifications are cancelled per day |
| time_base_freq_interact_cancel_notif_hr | Time-basedprobing : Number of notifications are cancelled per hour |
| time_base_freq_interact_no_resp_notif_all | Time-basedprobing : Number of notifications are not responded overall |
| time_base_freq_interact_no_resp_notif_day | Time-basedprobing : Number of notifications are not responded per day |
| time_base_freq_interact_no_resp_notif_hr | Time-basedprobing : Number of notifications are not responded per hour |
| time_base_freq_interact_ok_notif_all | Time-basedprobing : Number of notifications are responded/ok overall |
| time_base_freq_interact_ok_notif_day | Time-basedprobing : Number of notifications are responded/ok per day |
| time_base_freq_interact_ok_notif_hr | Time-basedprobing : Number of notifications are responded/ok per hour |
| time_base_overall_freq_incomplete_notifications_day_subject | Time-basedprobing : Number of notifications are incompleted per day/subject |
| time_base_overall_freq_incomplete_notifications_hr_day | Time-basedprobing : Number of notifications are incompleted per hr/day |
| time_base_overall_freq_notifications_day_subject | Time-basedprobing : Number of notifications are received per day/subject |
| time_base_overall_freq_notifications_hr_day | Time-basedprobing : Number of notifications are received per hr/day |
| time_base_overall_freq_notifications_hr_subject | Time-basedprobing : Number of notifications are received per hr/subject |
| time_base_total_freq_notif_all | Time-basedprobing : Number of notifications are received overall |
| time_base_total_freq_notif_day | Time-basedprobing : Number of notifications are received per day |
| time_base_total_freq_notif_hr | Time-basedprobing : Number of notifications are received per hour |

FIG. 6D

COGNITIVE BIAS DETECTION AND CORRECTION IN SELF-REPORTED DATA

BACKGROUND

One or more embodiments of the disclosure relate to cognitive bias detection and correction in self-reported data.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later.

According to an embodiment, a system is provided. The system includes a processor that executes computer-executable components stored in memory. The computer-executable components include first components that creates an ontology of bias descriptor features to identify cognitive biases. The cognitive biases include a combination of at least one device-induced cognitive bias, at least one testing-application-induced cognitive bias, or at least one study-design-induced cognitive bias.

According to another embodiment, a computer-implemented method is provided. The computer-implemented method includes generating, by a system operatively coupled to a processor, an ontology of bias descriptor features to identify cognitive biases. The cognitive biases include a combination of at least one device-induced cognitive bias, at least one testing-application-induced cognitive bias, or at least one study-design-induced cognitive bias.

According to a further embodiment, a computer program product for assessment of cognitive biases in self-reported data. The computer program product includes a computer-readable storage medium having program instructions embodied therewith, the program instructions executable by a processor to cause the processor to generate, by the processor, an ontology of bias descriptor features to identify cognitive biases. The cognitive biases include a combination of at least one device-induced cognitive bias, at least one testing-application-induced cognitive bias, or at least one study-design-induced cognitive bias.

BRIEF DESCRIPTION OF THE DRAWINGS

FIG. 4A illustrates a non-limiting example of predictive models for a target variable embodied in self-reported stress (SS), in accordance with one or more embodiments of this disclosure.

FIG. 4B illustrates a non-limiting example of a ranking of β features and α features, in accordance with one or more embodiments of this disclosure.

FIG. 6C illustrates non-limiting examples of β features and short description thereof, in accordance with one or more embodiments of this disclosure.

FIG. 6D illustrates other non-limiting examples of β features and short description thereof, in accordance with one or more embodiments of this disclosure.

DETAILED DESCRIPTION

Embodiments of the disclosure address the issue of detection and correction of cognitive biases in self-reported data. Embodiments of this disclosure can automatically detect and correct biases in target variables that are continuous, ordinal, or categorical. Correction of the bias can be performed, in some cases, by automatically updating the self-reported data. In addition, or in other cases, corrections of the bias can be performed by identifying explainable causes of the bias and then proposing suggestions to the design of the study and/or the device and software application used for data collection.

Some embodiments of this disclosure are described with reference to self-reported stress simply for the sake of illustration. The disclosure, however, is not limited in that respect. Indeed, the principles of this disclosure also can be applied to the self-reporting of data representative of quantities defining other types of physiological statuses or other quantities representative of particular events, such as expected waiting time in a queue.

Figure 1:
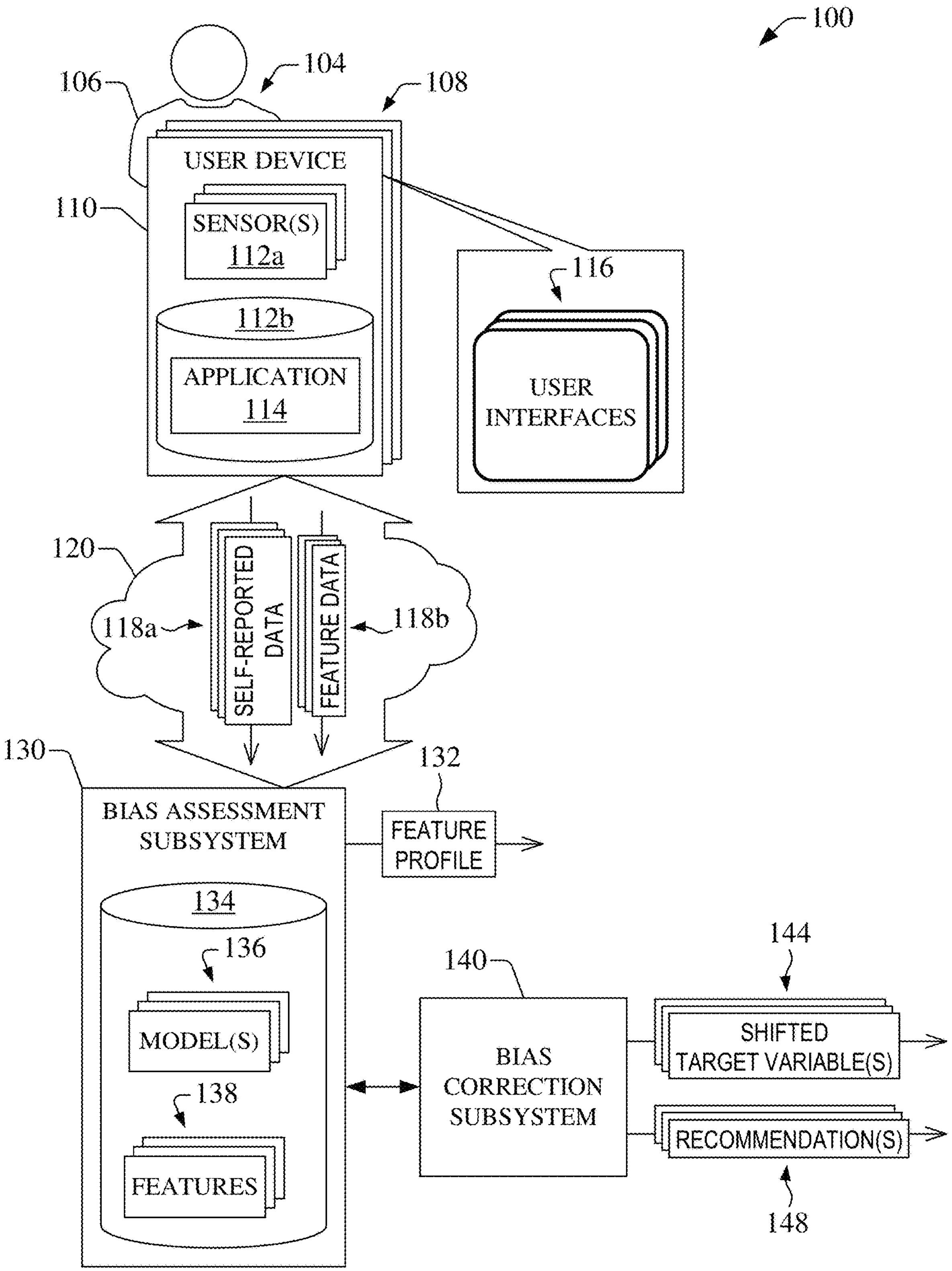
FIG. 1 illustrates a non-limiting example of an operational environment for cognitive bias detection and correction in self-reported data, in accordance with one or more embodiments of this disclosure.

With reference to the drawings, FIG. 1 illustrates a non-limiting example of an operational environment 100 for cognitive bias detection and correction in self-reported data, in accordance with one or more embodiments of this disclosure. The operational environment 100 includes multiple user devices 108 that can be operated by respective users 104. Each one of the multiple user devices 108 can be embodied a user device 110 that can be operated by a user 106 of the users 104. The user device 110 can be a computing device that can be portable or wearable. For example, the user device 110 can be a smart watch, a smart wristband, or similar wearable device. the user device can include one or several sensors 112*a* and one or several memory devices 112*b* (referred to as memory 112*b*). The memory 112*b* can retain a testing application 114 that can be executed by one or more processors (not depicted in FIG. 1) integrated into the user device 110, for example. The testing application 114 can be embodied in a software application, in some cases. The sensor(s) 112*a* and the testing application 114 in execution—individually or in combination—can probe one or several physiological quantities defining a state of the user 106. In one example embodiment, the user device 110 can include multiple optical sensors that can probe heart rate of the user 106, and the execution of the testing application 114 can cause the user device 110 to present indicia (visual and/or aural) identifying the heart rate. A display device (not depicted in FIG. 1) integrated into the user device 110 can present the indicia, for example.

Some raw data generated by at least one of sensor(s) 112*a* can be referred to as device data and can be indicative of first β features (also referred to as first bias descriptor feature(s)). Those first β features can be representative of aspects of a user device (e.g., user device 110, such as a smartwatch), the testing application 114, and/or a study design corresponding to a clinical study or another type of study conducted across the user devices 108.

Figure 2:
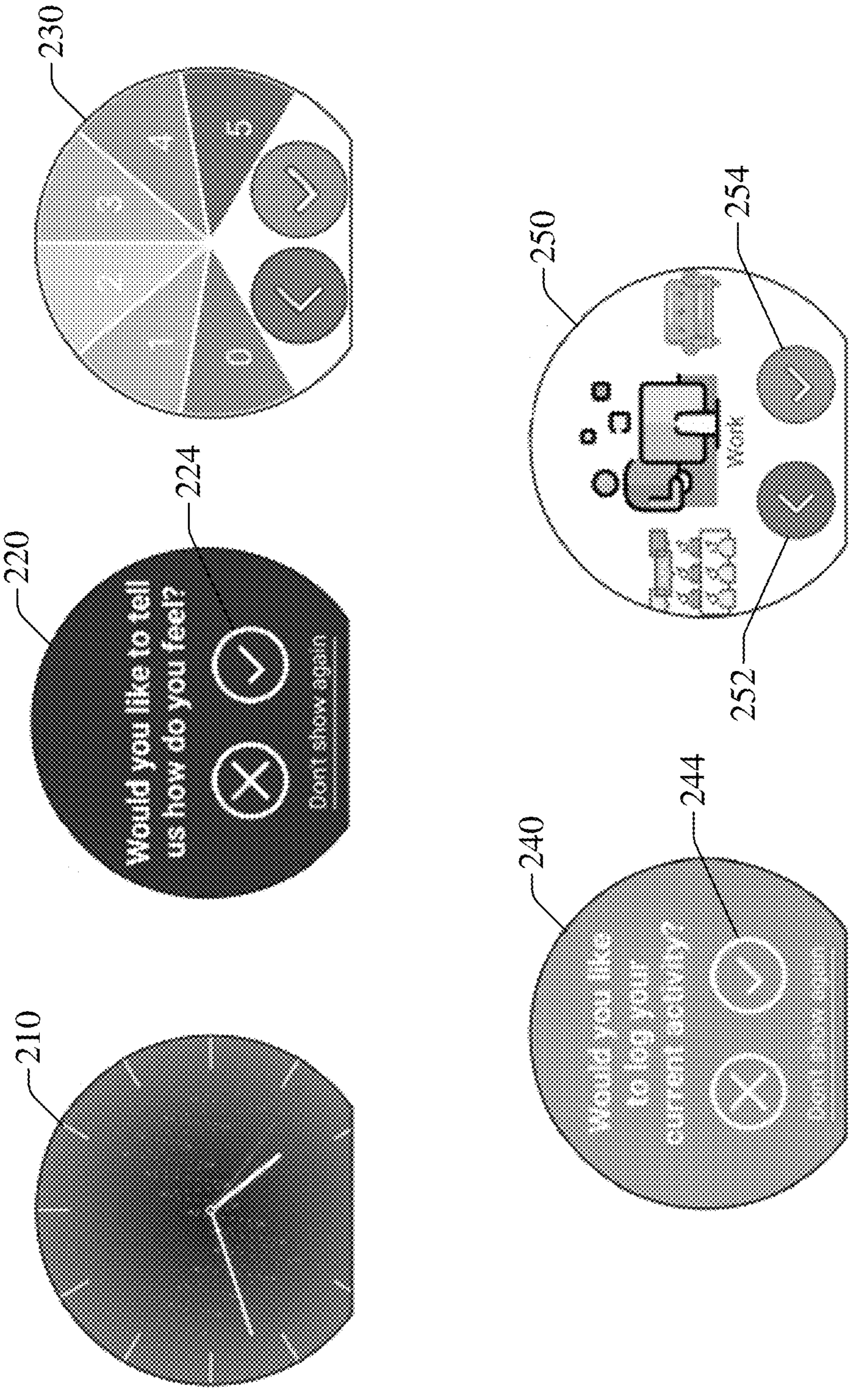
FIG. 2 illustrates non-limiting examples of user interfaces for self-reporting data, in accordance with one or more embodiments of this disclosure.

In some embodiments, execution of the testing application 114 can cause the user device 110 to present multiple user interfaces 116. The multiple user interfaces 116 can be presented in sequence, where a next user interface can be presented in response to interaction of the user 106 with a current user interface. At least one user interface (UI) in the sequence of the user interfaces 116 that is presented can permit accessing input data from the user 106. A portion of the input data can be representative of a physiological status (e.g., stress status) of the user 106. Simply for the sake of illustration, FIG. 2 illustrates multiple user interfaces that can constitute the sequence of user interfaces 116 in an example embodiment in which the physiological status is embodied in stress status and the user interface 110 is embodied in a smartwatch.

More specifically, the multiple UIs include a user interface 210 that the smartwatch can present when idle. Additionally, the smartwatch can present the user interface 220 to prompt the user 106 to report data. The user interface 220 includes a selectable visual element 224 that, when selected, causes the smartwatch to present the user interface 230. The user interface 230 can include six selectable visual elements that permit providing a selection of a stress level (e.g., 0, 1, 2, 3, 4, or 5). After presentation of the user interface 230, the smartwatch can present the user interface 240. In one aspect, the user interface 240 includes a selectable visual element 244 that, in response to being selected, can cause the smartwatch to present the user interface 250. The user interface 250 can include a selectable visual element 252 that can permit selecting a defined activity by navigating a carousel of icons, each representing an activity (working, making a presentation, relaxing at home, or similar activity). After navigating to a particular icon representing a desired activity, selection of a selectable visual element 254 can cause the smartwatch to send data indicative of that activity.

With further reference to FIG. 1, because the input data is received from the user 106, at least the portion of the input data can embody self-reported data 118. The self-reported data 118*a* can be structured and can defined one or a combination of a continuous variable (e.g., anticipated waiting time in a queue); an ordinal variable (e.g., perceived stress level on a scale of multiple discrete levels, such as 0 to 5); a categorical variable (e.g., a mood type selected from a mood palette).

Another portion of the input data can define second β features (also referred to as second bias descriptor feature(s)) representing objective behavioral measurements collected by the user device 110 and the testing application 114 in response to a study and study design thereof. Those second β features, individually or in a particular combination, can identify interaction of the user 106 with (i) the user device 110 (e.g., the number of times a button is pushed), (ii) the testing application 114 (e.g., dwelling time on a certain screen), and (iii) components of a study (e.g., response time to an intervention in a clinical study).

Yet another portion of the input data can define third β features (also referred to as third bias descriptor features) representing subjective experience measurements collected via surveys, questionnaires, interviews, and/or other self-reported methods. Those third β features can quantify perception of the user 106 of their interaction(s) with the device (e.g., comfort of wearing a smartwatch), the testing application 114 (e.g., ease-of-use of the application), and component(s) of the study (e.g., length of participation).

At least one of the user interfaces 116 presented in the sequence of user interfaces can cause the user device 110 to send the self-reported data 118. As is illustrated in FIG. 1, the user device 110 can send the self-reported data 118 to a bias assessment subsystem 130 via one or more networks 120. The network(s) 120 can include at least one wireless network, at least one wireline network, or a combination thereof.

Table 1 illustrates device data and input data in embodiments in which stress level can be monitored using the user device 110. The device data and the input data are represented collectively as feature data 118*b*.

TABLE 1

Examples of device data and input data and respective sources

| | Device | Behavioral/Cognitive | Behavioral/Cognitive Data Source |
|---|---|---|---|
| Stress | Heart rate variability (HRV) (a quantity having values within [−1, 1]) | Perceived stress levels (e.g., 0 to 5) | Smartwatch UI data set |
| Motion | Accelerometer Gyroscope | (May be inferred from event logs.) | Smartwatch UI data set |
| Battery | Battery levels | N/A | N/A |
| Stress logging | Event-based (frequency, association with HRV) | Perceived frequency of interaction with | Exit survey |

TABLE 1-continued

Examples of device data and input data and respective sources

| | Device | Behavioral/Cognitive | Behavioral/Cognitive Data Source |
|---|---|---|---|
| | Time-based (frequency) | notifications | |
| | User initiated (may associate with events and perceived stress) | Perceived frequency of notifications | |
| | | Proposed frequency of notifications | |
| | | Perceived difficulty of expressing stress levels | |
| | | Perceived consistency of expressing stress levels | |
| | | Proposed stress expression | |
| Event logging | Event-based | Perception of events | Exit survey |
| | Time-based | Proposed events | |
| | User initiated | Retrospective stress rating (training) | |

The bias assessment subsystem 130 can receive the self-reported data 118*a* and the feature data 118*b*. The feature data 118*b* can be indicative of a defined group of β features $\{\beta_1, \beta_2, \ldots \beta_{N-1}, \beta_N\}$, where Nis natural number greater than unity.

In response to receiving such data, the bias assessment 130 can evaluate a group of cognitive biases. Each cognitive bias in the group of cognitive biases is n β feature. Thus, the group of cognitive features can include at least one β feature. In some embodiments, the group of cognitive features is embodied in multiple β features. Further, α features also can influence the self-reported data 118*a*. Rather than being determined by behavioral measurements or experiential measurements, as is the case of β features, α features can be configured prior to data collection corresponding to a particular study. For purposes of illustration, there can be two types of α features: (I) First α features representing respective main effects assessed in a study. In cases where the study is an observational study, main effects are defined by respective variables hypothesized to have an effect on a target variable (denoted as Y, simply for the sake of nomenclature). In other cases where the study is an intervention study, main effects are defined by respective variables tested in the intervention. In the intervention study, participants receive interventions according to a defined research plan and/or protocol. The interventions can include medical products, such as drugs or medical devices; procedures; or changes to participants' behavior, such as diet. (II) Second α features (referred to as confounders or confounding factors) corresponding to respective dimensions and/or measures in a data model that defines the study. Two examples of confounders are age and gender. As an example, a study that examines the effect of a learning mobile application can control for age and gender. In that study, usage of the learning mobile application can be a main effect, and self-reported learning efficacy can embody the target variable Y. The testing application 114 can embody the learning mobile application in that example.

Figure 3:
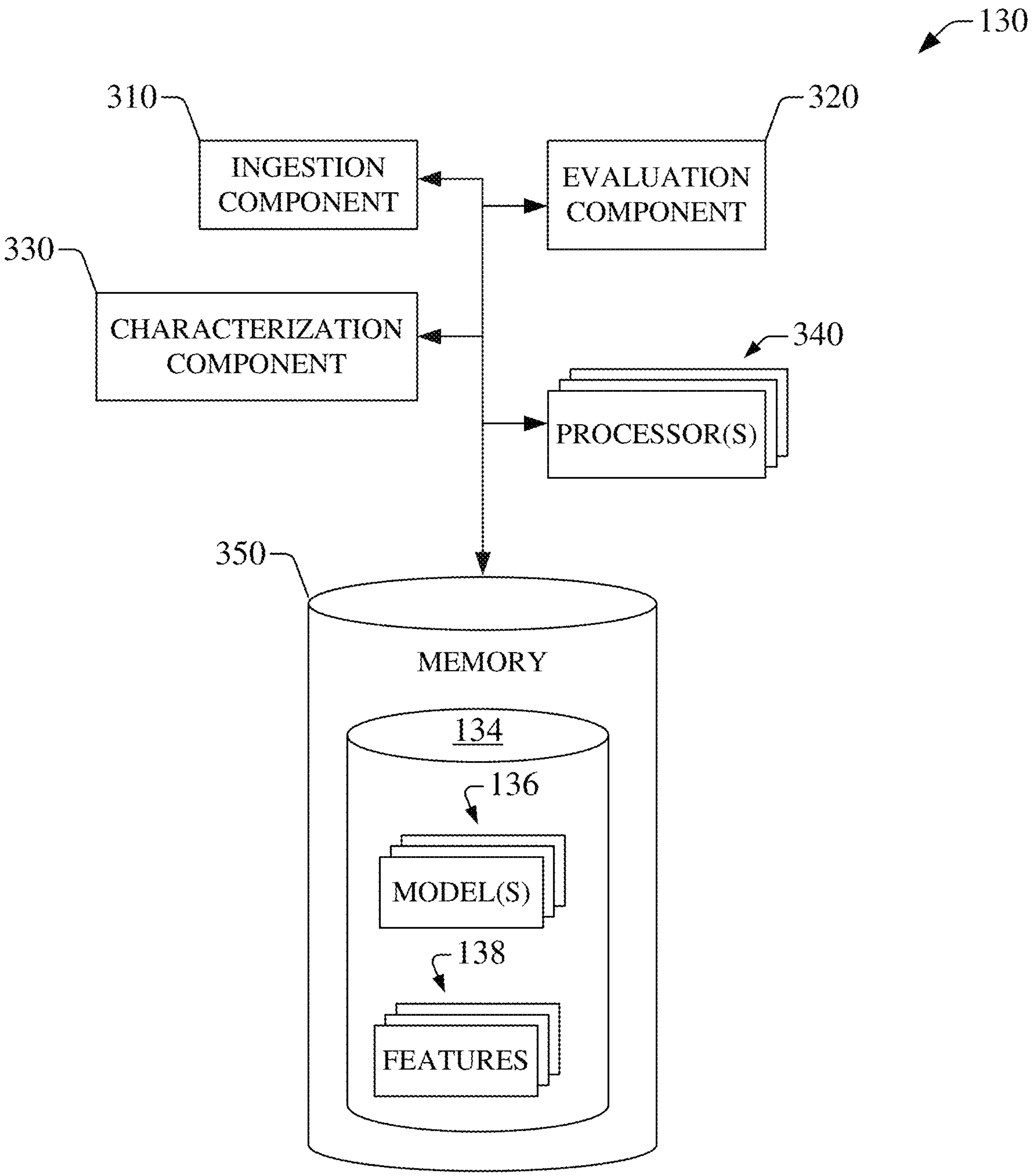
FIG. 3 illustrates a non-limiting example of a subsystem for the detection of cognitive bias in self-reported data, in accordance with one or more embodiments of this disclosure.

In some embodiments, as is shown in FIG. 3, to evaluate a group of cognitive biases, the bias assessment subsystem 130 can include an ingestion component 310 that can access the self-reported data 118 and the feature data 118*b*. Further to that end, the bias assessment subsystem 130 also can include an evaluation component 320 that can measure the group of cognitive biases present in the self-reported data 118 that is accessed. More specifically, in some cases, the evaluation component 320 can measure, using a collection of predictive models 136 (FIG. 1), an individual efficacy of each one of the β feature(s) in inducing one or more cognitive biases corresponding to respective bias descriptor feature(s). Such efficacy can be referred to as "impact." An impact can have a size and/or a direction. Size refers to magnitude of the impact, and direction refers to sign (positive or negative) of the impact. To that end, in some embodiments, the collection of predictive models 136 includes a particular predictive model that has an overall model performance P in predicting the target variable Y using the defined group of β features $\{\beta_1, \beta_2, \ldots \beta_{N-1}, \beta_N\}$ as a feature vector. For purposes of illustration, the model performance P is the accuracy of the predictive model. Thus, the model performance P can be quantified by one of many metrics, including $R^2$, root mean square error (RMSE), mean absolute error (MAE), or mean absolute percentage error (MAPE), for example. In cases in which the particular predictive model is a binary classification model, the model performance P can be quantified by one of the following metrics: area-under-curve (AUC) under receiver operator characteristic (ROC), F1-score, or precision recall, for example. The defined group of β features is quantified by the feature data 118*b*; that is, the feature data 118*b* specifies the defined group of β features. Still further to that end, the collection of predictive models 136 also includes a first group of predictive models, each predictive model in that first group being trained to model the target variable Y using all but one particular β feature in the defined group of β features. That is, for a group of β features $\{\beta_1, \beta_2, \ldots \beta_{N-1}, \beta_N\}$, each predictive model in first group can be trained to predict the target variable Y using N−1 features $\{\beta_1, \beta_2, \ldots \beta_{i-1}, \beta_{i+1} \ldots \beta_{N-1}, \beta_N\}$ with $1 \le i \le N$ and $\beta_i$ being the β feature that is removed. Each predictive model trained using N−1 features has a respective model performance $p_i^{(-)}$, and the impact of the removed β feature $\beta_i$ can be defined as $\omega_i = P - p_i^{(-)}$.

In other cases, the evaluation component 320 can measure, using the collection of predictive models 136, a collective impact of at least a subset of the bias descriptor features in inducing such one or more cognitive biases. More specifically, in one configuration, the collection of predictive models 136 includes a defined predictive model that is trained without β features. Hence, that defined predictive model can be trained using α features exclusively and has a model performance $p_0$. The impact $\omega_0 = P - p_0$ defines the effect of all β features in the self-reported data 118*a*.

In another configuration, the collection of predictive models 136 includes a second group of predictive models, each predictive model in that second group being trained to model the target variable Y using all but subset of the defined group of β features. That is, for the defined group of β features $\{\beta_1, \beta_2, \ldots \beta_{N-1}, \beta_N\}$, each predictive model in second group can be trained to predict the target variable Y using N-m features $\{\beta_1, \beta_2, \ldots \beta_{i-m-1}, \beta_i \ldots \beta_{N-1}, \beta_N\}$ with $1<m<N$ and $\beta_{i-m}$, $\beta_{i-m+1}, \ldots \beta_{i-1}$ being the β features that are removed. Such a subset can be referred to as a construct. The construct can be a group of β features related to a particular concept, e.g., the construct "familiarity" may include β features such as "time spent to complete a task", "number of attempts to complete a task", "number of screens viewed when completing a task", "dwelling time on task interface", and the like. For a total number M of constructs, respective impacts $\omega_k$ can be determined as $\omega_k=P-p_k^{(-)}$ where k is an index that identifies one of the M constructs.

Simply as an illustration, the target variable Y can be embodied in self-reported stress (SS), and the second group of predictive models can include the models shown in FIG. 4A. Each one of those models relate the target variable Y (e.g., SS) to other features applicable to the study, such as user interface (UI), heart rate variability (HRV) prior to receiving a notification to provide information on how participant feels (referred to as HRV1), HRV after receiving a notification to provide such information (referred to as HRV2), and HRV after logging an activity (referred to as HRV3), exit survey (ES), event (E), date and time (T), age and gender (D), personality (P), Further, the bias assessment subsystem 130 also can include a characterization component 330 that can identify one or more of a second attribute of the device, a second attribute of the testing application 114, or a second attribute of study design inducing one or more cognitive biases of the group of cognitive biases.

As a result of the evaluation of the group of cognitive biases, the bias assessment subsystem 130 can supply a feature profile 132 identifying β features corresponding to cognitive biases in the group of cognitive biases and further identifying impacts corresponding to the cognitive biases. The feature profile 132 also can identify α features. The characterization component 330 can generate the feature profile 132. As part of generating the feature profile 132, the characterization component 330 can rank the evaluated cognitive biases (including a features) in decreasing order of impact. Simply as an illustration, FIG. 4B presents a schematic chart of a ranking 400 of impact of an example set of β features $\{\beta_1, \beta_2, \beta_3, \beta_4, \beta_5, \beta_6, \beta_7, \beta_8\}$ and an example set of α features $\{\alpha_1, \alpha_2, \alpha_3, \alpha_4, \alpha_5, \alpha_6\}$. Two α features, $\alpha_5$ and $\alpha_6$ (marked with arrows in FIG. 4B), represent respective main effects. In one example, as represents HRV1 and $\alpha_6$ represents HRV2. Without intending to be bound by modeling, because at least some β features rank higher than main effects in the ranking 400, the hypothesized relationship between main effect (e.g., heart rate variability (HRV)) and target variable (e.g., self-reported stress) is influenced by experience of the user 106 during the study. More specifically, the ranking 400 conveys that $\beta_6$ and $\beta_8$ have significant impact on the target variable.

In cases where β features influence the relationship between main effect and target variable, embodiments of this disclosure can permit removing that influence by removing of β features from a first model of the model(s) 136. To that end, as is illustrated in FIG. 1, the operational environment 100 can include a bias correction subsystem 140. As mentioned, each one of the model(s) 136 have a satisfactory performance (best performance, second best performance, etc.). For the first model, the bias correction subsystem 140 can apply the target variable and a group of β features to generate one or more shifted target variables 144 corresponding to respective differences between a target variable and the group of β features. The shifted target variable(s) 144 are thus corrected for bias descriptors corresponding to at least one of the multiple user devices 108, the testing application 114, or study design.

In cases where the first model is embodied in a regression model (e.g., multivariate linear regression, lasso regression, logistic regression, ordinal regression, or similar), a parameterization of the first model is available to determine the shifted target variable(s) 144. In those cases, the bias correction subsystem 140 can use the parameterization to adjust self-reported data 118 defining a target variable. In other cases where the first model is a machine-learning model (e.g., a neural network model or a random forest model, a K-nearest neighbor (KNN) model, a support vector machine (SVM), or similar model), the bias correction subsystem 140 can generate a mathematical expression representative of the first model. The bias correction subsystem 140 can then apply the mathematical expression, or a parameterization thereof, to adjust self-reporting data 118 defining a target variable.

Figure 5:
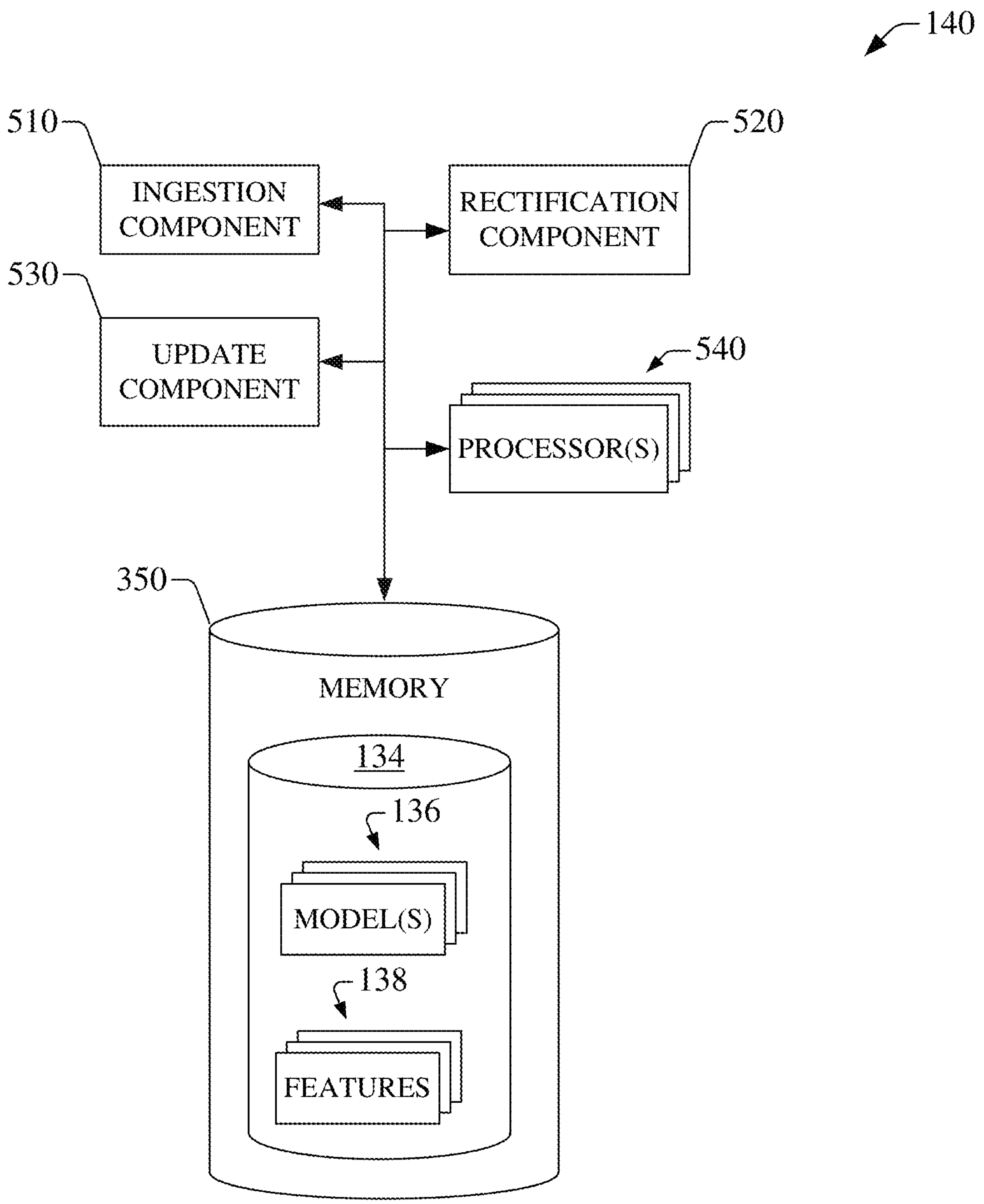
FIG. 5 illustrates a non-limiting example of a subsystem for the correction of cognitive bias in self-reported data, in accordance with one or more embodiments of this disclosure.

In some embodiments, as is illustrated in FIG. 5, the bias correction subsystem 140 can include a rectification component 520 that can correct one or more induced cognitive biases by adjusting existing self-reported data 118 defining a target variable. Adjusting the existing self-reported data 118 can include removing a particular cognitive bias of the one or more induced cognitive biases from the existing self-reported data 118. In those embodiments, the bias correction subsystem 140 also can include an update component 530 that can cause, based on at least one bias descriptor feature, a change to at least one of the user device 110, the testing application 114, or the study design.

In addition, or in some embodiments, the bias correction subsystem 140 can generate one or several β-feature recommendations 148 for modifications to a design of the testing application 114, the user device 110, and/or study procedure used in the study. In one embodiment, the update component 530 can generate the recommendation(s) 148. Simply as an illustration, to correct for a familiarity-related β feature in a UI (e.g., one of the user interfaces 116) and study design, the update component 530 can generate a recommendation for participants to receive additional training; a second recommendation for the UI to display additional events in a single pane on a screen of a display device of the user device 110; and/or a third recommendation for real time access to explanations of events incorporated into the testing application 114.

Figure 6A:
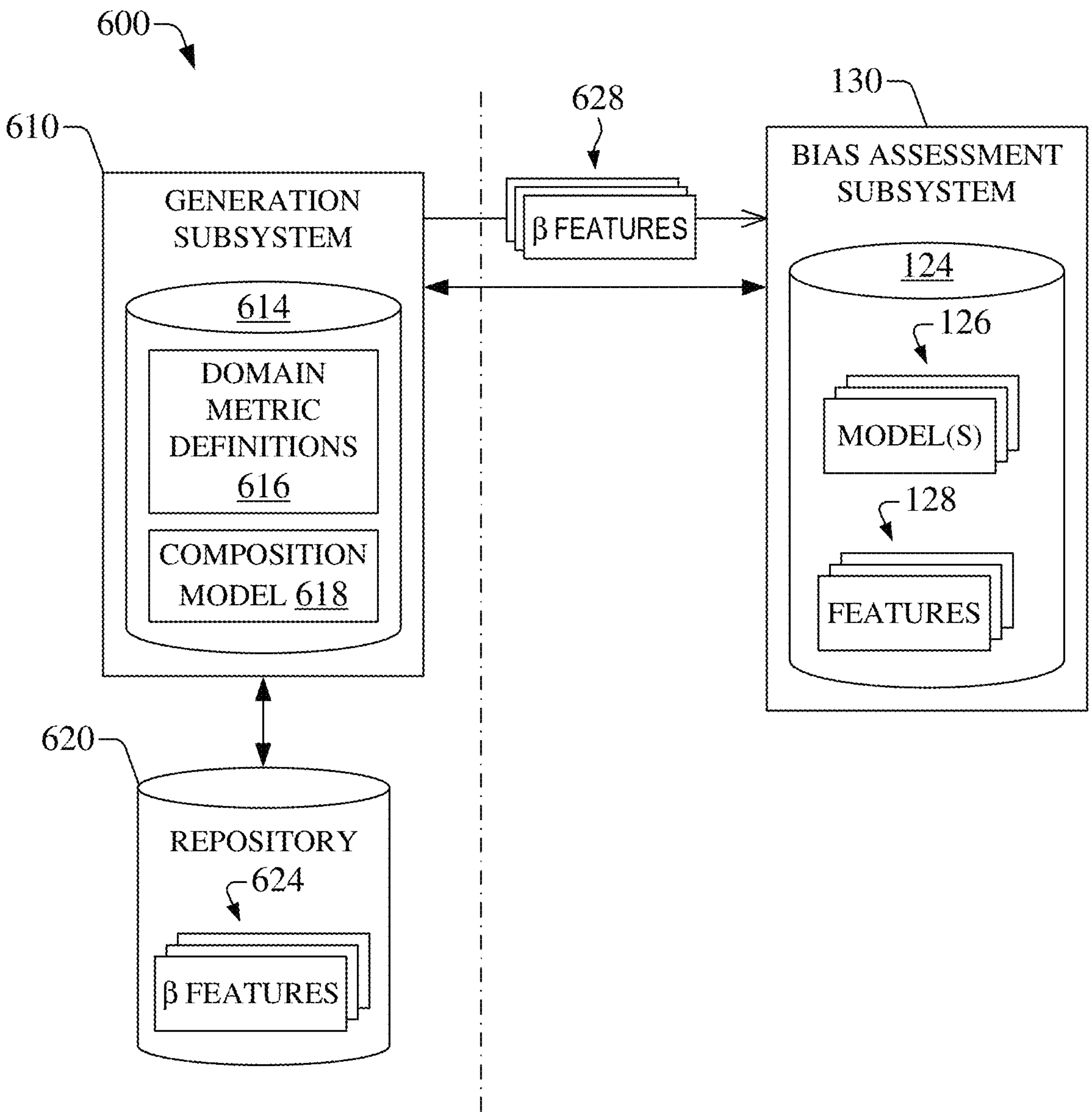
FIG. 6A illustrates a non-limiting example of a system for creation of an ontology of β features, in accordance with one or more embodiments of this disclosure.
Figure 6B:
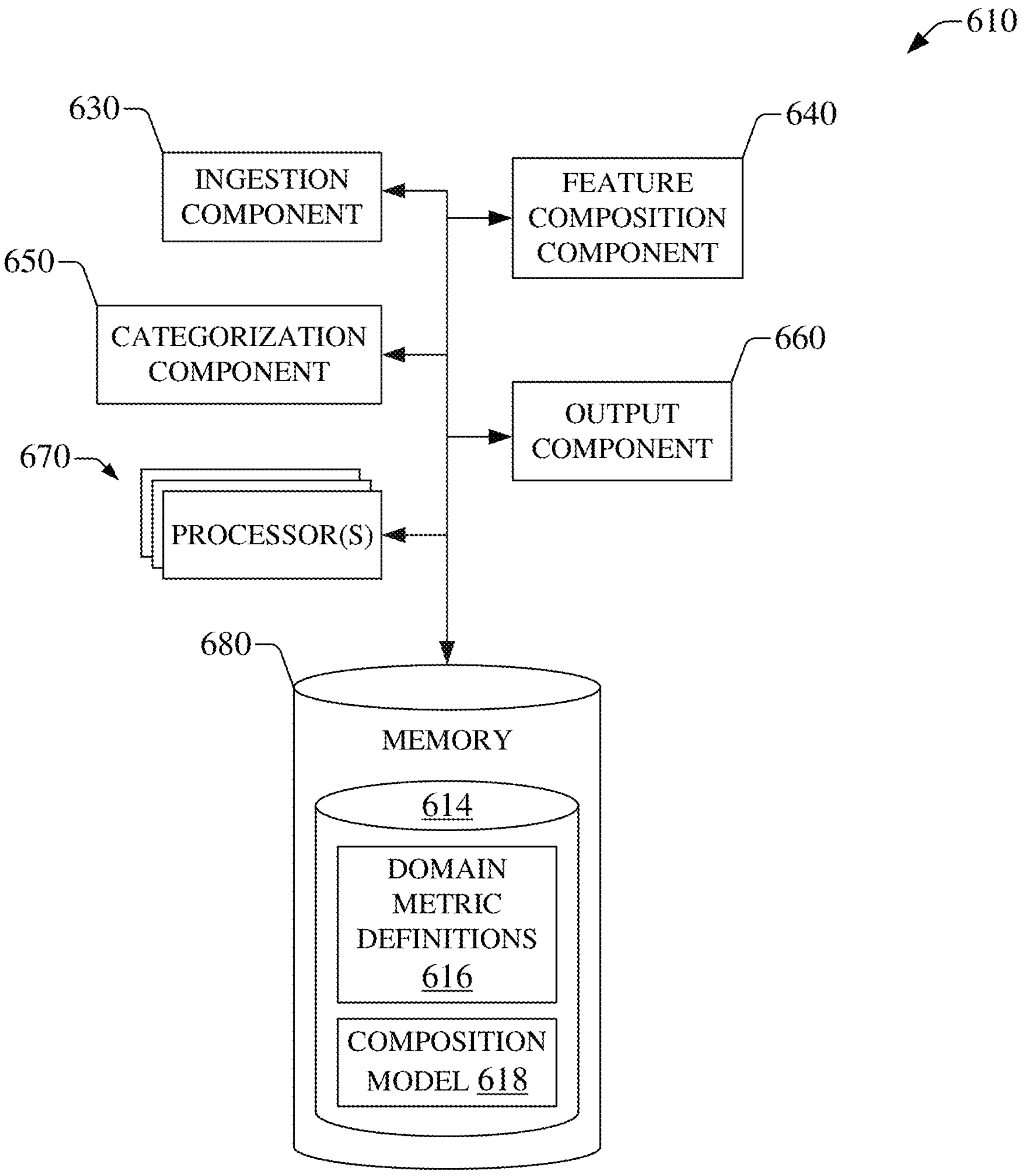
FIG. 6B illustrates a non-limiting example of a subsystem for the detection of cognitive bias in self-reported data, in accordance with one or more embodiments of this disclosure.

FIG. 6 illustrates an example of a system 600 for creation of an ontology of β features (or, as mentioned, bias descriptor features), in accordance with one or more embodiments of this disclosure. The exemplified system 600 includes a generation subsystem 610 that can create the ontology of bias descriptor features. To that end, the generation subsystem 610 can access definitions of respective domain metrics. Such definitions can be based on available raw data (e.g., device data or input data) for a study across multiple user devices (e.g., multiple user devices 108). Without intending to be bound by nomenclature, raw data refers to data generated by a user device, or another type of device, used to conduct the study and/or data accessed by the user device, or that other type of device. A definition of a domain metric specifies a metric quantified by raw data obtained during the course of the study. A domain metric can pertain to domain knowledge of a study design and/or domain knowledge of user interface design. In some cases, the generation subsystem 610 can access the definitions from a catalog of domain metric definitions 616 retained in one or more memory devices 614 (also referred to as memory 614). In other cases, the generation subsystem 610 can receive the definitions from another subsystem or component thereof (neither one depicted in FIG. 6A) remotely located relative to the generation subsystem 610. In some embodiments, as is shown in FIG. 6B, the generation subsystem 610 can include an ingestion component 630 that can access those definitions regardless of the manner of accessing the definitions of respective domain metrics. Table 2 illustrates an example of the catalog of domain metric definitions 616 that are available in a self-reported stress (SS) study wherein the multiple user devices 108 are embodied in smartwatches. As is illustrated in Table 2, the catalog of domain metric definitions 616 can be organized in categories, regardless of the particular type of study associated with such definitions. In one example, the categories can include "System Features," "Behavioral/cognitive Features," "Participant Features," and "Time."

TABLE 2

| Example domain metrics quantified using available raw data |
|---|
| System Features |
| HRV (sensor) |
| Motion data (sensor) |
| Perceived stress level log (smartwatch participant reported) |
| Event log (smartwatch participant reported) |
| Session initiation methods (i.e., event based - when stress is detected, time based - random, user initiated) (smartwatch UI) |
| Battery levels (smartwatch UI) |
| Behavioral/cognitive Features |
| Screen on/off (smartwatch UI) |
| Data entry behavior (e.g., timing, scrolling patterns, skipping patterns) (smartwatch UI) |
| Perceived frequency of interaction with notifications (exit survey) |
| Perceived frequency of notifications (exit survey) |
| Proposed frequency of notifications (exit survey) |
| Perception of events (exit survey) |
| Proposed events (exit survey) |
| Perceived difficulty of expressing stress levels (exit survey) |
| Perceived consistency of expressing stress levels (exit survey) |
| Proposed stress expression (exit survey) |
| Other (free text comments) |
| Retrospective stress rating (training) |
| Participant Features (Static Metrics During Study) |
| Age (entry survey) |
| Gender (entry survey) |
| Personality (5 dimensions, for example) (entry survey) |
| Time |
| Total hours of data collected (smartwatch UI) |
| hours (smartwatch UI) |
| minutes (smartwatch UI) |
| seconds (smartwatch UI) |
| days (smartwatch UI) |

As is described herein, the bias descriptor features can be used to identify cognitive biases including a combination of at least one device-induced cognitive bias, at least one testing-application-induced cognitive bias, or at least one study-design-induced cognitive bias. A first one of the bias descriptor features in the ontology can represent an attribute of a device, an attribute of a testing application, or an attribute of study design affecting a state of the user 106, or a combination of those attributes. A second one of the bias descriptor features in the ontology can represent a user behavior and/or a user experience of the user 106 in response to the study design.

Further, to create the ontology of beta features, the generation subsystem 610 can apply a composition model 618 to the definitions of domain metrics that have been accessed. The composition model 618 can embodied in a machine-learning model or a genetic algorithm model that is trained to generate multiple bias descriptor features. The composition model 618 can be trained using a large corpus of human-generated ontologies for numerous types of studies and catalogs of domain metrics. The composition model 618 can be retained in the memory 614. In some embodiments, as is shown in FIG. 6B, the generation subsystem 610 can include a feature composition component 640 that can generate multiple β features by applying the composition model 618 to the accessed definitions of domain metrics. In an example case in which the composition model 618 is a machine-learning model, output of the application of composition model 618 can include confidence scores for respective ones of the multiple β features that have been generated. Thus, the feature composition component 640 can select a subset of the multiple β features, where each one of the β features in the subset can have a confidence score that is equal to or greater than a threshold value. The selected subset can constitute the ontology of β features.

Further, in an example case in which the composition model 618 is embodied in a genetic algorithm, the application of the classification model 618 to the accessed definitions of domain metrics can result in multiple sets (or generations) of β features that converge to a satisfactory set (or generation) of β features, each having a fitness score that exceeds a threshold value. The satisfactory generation of β features constitute the ontology of β features. In such a case, a next generation of β features can arise from a particular combination of at least one prior generation of β features. For a prior generation, β features having a fitness score that is less than the threshold value can be discarded before forming a next generation of β features. Without intended to be bound by modeling, a fitness score of a beta feature can be determined by a similarity metric between the beta feature and another beta feature known to be applicable to a study that is similar to the study for which the ontology of β features being created.

After a satisfactory (in terms of confidence scores or fitness scores, for example) set of multiple β features, the generation subsystem 610 can categorize the set of multiple β features to form the ontology of β features. Categorization can be implemented by determining similarly metrics between pairs of β features for example.

The generation subsystem 610 can retain that ontology within one or several memory devices 620 (referred to as repository 620). The ontology can be retained as a collection of multiple β features 624 organized in one or several categories. Such a collection can be referred to as an ontology. An example ontology of β features retained in the repository 620 is illustrated in Table 3.

TABLE 3

| Example Ontology of Bias Descriptor Features |
|---|
| Stress |
| HRV |
| HRV (e.g., 1 minute window) before probing |
| HRV immediately after probing |

TABLE 3-continued

| Example Ontology of Bias Descriptor Features |
|---|
| Difference between HRV before and after probing |
| Perceived stress levels |
| HRV and perceived stress level discrepancy |
| Stress labeling |
| Perceived difficulty of expressing stress levels |
| Perceived consistency of expressing stress levels |
| Probing |
| Event-based probing (time series) |
| Event-based probing frequency overall/per day/per hour |
| Average |
| Min |
| Max |
| Time-based probing (time series) |
| Time-based probing frequency overall/per day/per hour |
| Average |
| Min |
| Max |
| Response to probing |
| Participants' responsiveness to probing (The time between probing and stress logging; OR 3: very responsive - stress logged within 1 minute of probing; 2: somewhat responsive - stress logged within 5 minutes of probing; 1: not responsive - stress logged eventually for this probing event; 0: absent - stress not logged for the probing event) |
| Participants' attentiveness to probing (The time between probing and when watch is turned on; OR 3: very attentive - watch turned on within 1 minute of probing; 2: somewhat attentive - watch turned on within 5 minutes of probing; 1: not attentive - watch turned on before the next probing event; 0: absent - watch not turned on before the next probing event) |
| Frequency of responses to event-based/time-based probing (time series of 0-no response and 1-responded for each probing; OR expressed in percentage for each person overall/per day/per hour) |
| User initiated logging (user-initiated logging event and associated time stamp) |
| Perceived frequency of interaction with notifications |
| Objective openness to receiving more notifications (proposed frequency of notifications - actual notification frequency (i.e., event-based + time-based probing)) |
| Discrepancy in perceived and objective openness to receiving more notification (calculate x = [proposed frequency of notifications - actual notification frequency (i.e., event-based + time-based probing)], values could be >0, = 0, or <0; y = perceived frequency of notifications; normalize x and y; compare x and y) |
| Stress logging |
| Dwelling time on stress logging intro page |
| Dwelling time on stress logging page |
| The number of hours it took for the participant to click on the "Don't show again" button for each screen |
| Whether participant completed stress logging |
| How many times the participant completed the logging/responded to the probing out of all the instances of probing |
| Event logging |
| Participants' familiarity with event labeling (scroll through 1 direction - familiar; scroll both directions - unfamiliar; or a continuous variable of steps taken versus steps needed to get to the final entry) |
| Dwelling time on event logging intro page |
| Dwelling time on event logging page |
| The number of hours it took for the participant to click on the "Don't show again" button for each screen |
| Whether participant completed event logging |
| How many times the participant completed the logging out of all the instances of probing |
| General behavior |
| Participant's familiarity with watch use (number of times user switched watch face during each logging. When users switch watch face, a new UI file is created) |
| Session time (time spent from turning on watch face to completing event logging) |
| Perception of system elements |
| Perceived frequency of notification |
| Proposed frequency of notifications |
| Perception of events |
| Proposed events |
| Time |
| Minute of hour |
| Hour of day |
| Day of week |
| Minutes since previous probing |
| Minutes since previous interaction |

Other β features that can constitute the collection of multiple β features 624 include the example β features 685 shown in FIG. 6C and/or the example β features 695 shown in FIG. 6D, in accordance with one or more embodiments of this disclosure.

After creating the ontology of β features, the generation subsystem 610 can supply at least a subset 628 of the collection of β features 624 to the bias assessment subsystem 130. In some embodiments, the generation subsystem 610 can include an output component 660 (FIG. 6B) that supply at least the subset 628. In addition, or in some embodiments, the output component 660 can generate a graphical representation of the ontology of β features. An example of the graphical representation is a graph including nodes corresponding to respective categories and subcategories, and edges connecting the nodes. The output component 660 can cause a display device (not depicted in FIG. 6B) to present the graphical representation. In some case, the graphical representation that is presented can be edited using input data. An edited version of the graphical representation can cause the generation subsystem 610 to update the features 624. For instance, the ingestion component 630 can receive input data defining one or more changes to the ontology of β features. The categorization component 650, for example, can receive the input data and can update the β features 624 according to the one or more changes.

Figure 7:
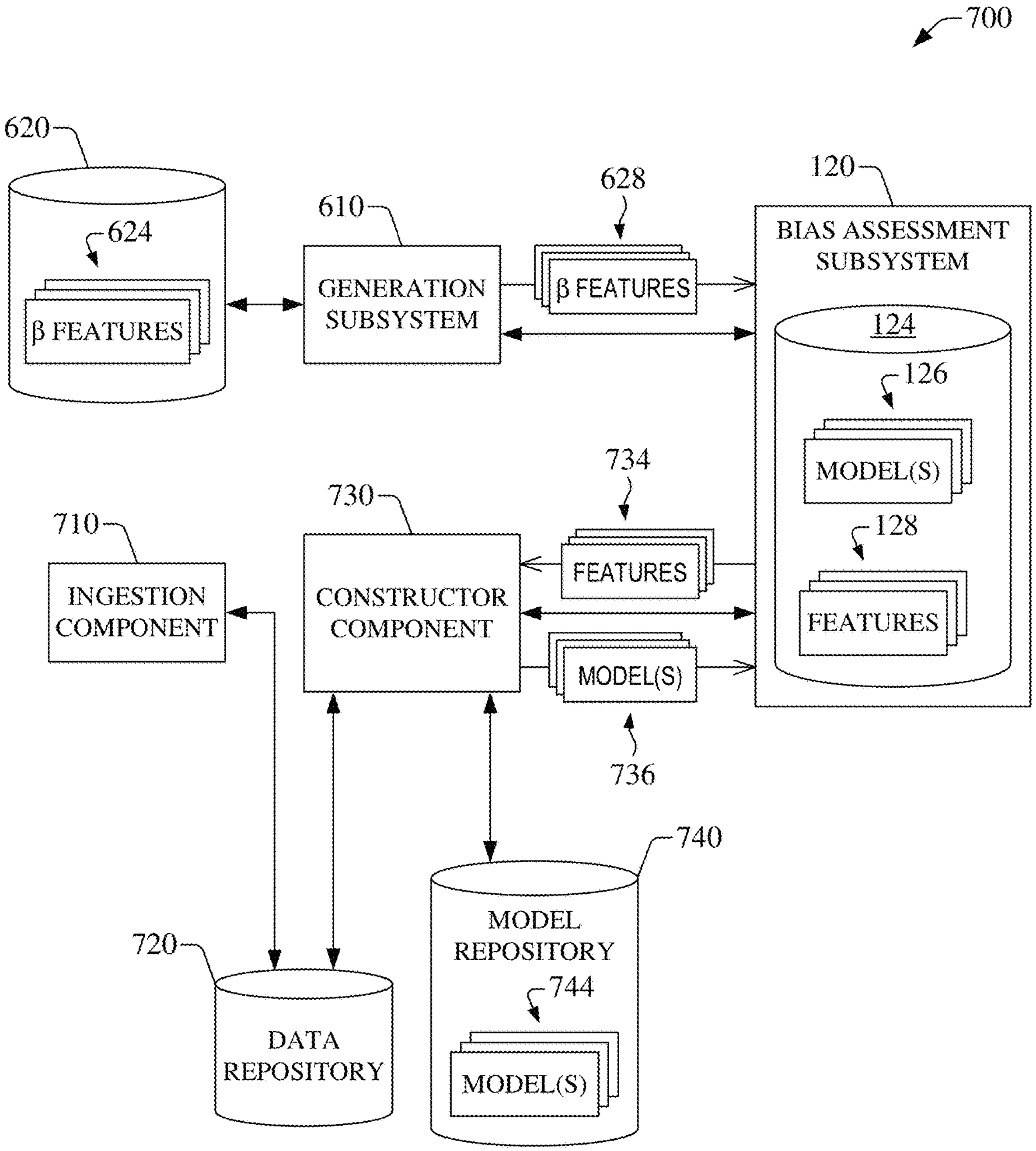
FIG. 7 illustrates a non-limiting example of a system for construction and selection of a predictive model that can be used to detect one or more cognitive biases, in accordance with one or more embodiments of this disclosure.

FIG. 7 illustrates an example of a computing system 700 for construction of a predictive model that can be used to detect one or more cognitive biases, in accordance with one or more embodiments of this disclosure. Although the exemplified computing system 700 contains the computing system 600 (FIG. 6), the disclosure is not limited in that respect. The computing system 700 includes an ingestion component 710 that can access self-reported data corresponding to a target variable. For example, the target variable can be embodied in self-reported stress level. Accordingly, the target variable can be an ordinal variable having one of several defined values. The self-reported data can be accessed (e.g., received) from multiple user devices, such as a smartwatch or another type of suitable computing device.

The ingestion component 710 can retain the self-reported data in one or more memory devices 720 (referred to as data repository 720). The self-reported data retained in the data repository 720 and constitutes training data to generate a predictive model in accordance with aspects described herein. As mentioned, the predictive model can be a machine-learning model or a statistical model.

The computing system 700 also includes a constructor component 730 that can operate on the training data retained in the data repository 720 and multiple features 734. The multiple features 734 can include at least a subset of the multiple features 128 and, thus, the multiple features 734 can include a combination of α features and β features. In one example configuration, the features 734 include 11 alpha features and 66 β features. The 11 alpha features can include physiological stress levels, reported event name; day of week; hour of day; age; gender; and personality type. Here personality type includes several features: Extravert vs. Introvert (E-I), Judgment vs. Perception (J-P), sensing vs. intuitive (S-N), assertive vs. turbulent (A-T), and thinking vs. feeling (T-F). Such 66 β features can include the example β features 685 illustrated in FIG. 6C and example β features 695 illustrated in FIG. 6D. Short descriptions 687 of respective β features 685 also are shown in FIG. 6C. Additionally, short descriptions 697 of respective β features 695 also are shown in FIG. 6D.

By operating on the training dataset, the constructor component 620 can determine a solution to an optimization problem with respect to a prediction error function. The form of that function is specific to the type of the predictive model (machine-learning model or statistical model). Regardless of its form, the prediction error function yields a value based on an evaluation of differences between known values of the target variable and predicted values of the target variable. The constructor component 730 can determine the predicted values by applying a current iteration (or current version) of the predictive model to α features vector. The feature vector includes multiple items and each item is a β feature or an a feature.

The solution to the optimization problem arises from converging to a set of model parameters that minimizes the prediction error function. The set of model parameters defines a trained predictive model. Accordingly, the constructor component 730 can train one or many predictive models 744 and can then retain the trained predictive model(s) 630 in one or several memory devices 740 (referred to as model repository 740).

The constructor component 730 can supply a group of trained predictive models 736 to the bias assessment subsystem 120. In response bias assessment subsystem 120 can retain the group of trained predictive models 736 as part of the model(s) 126.

Figure 8A:
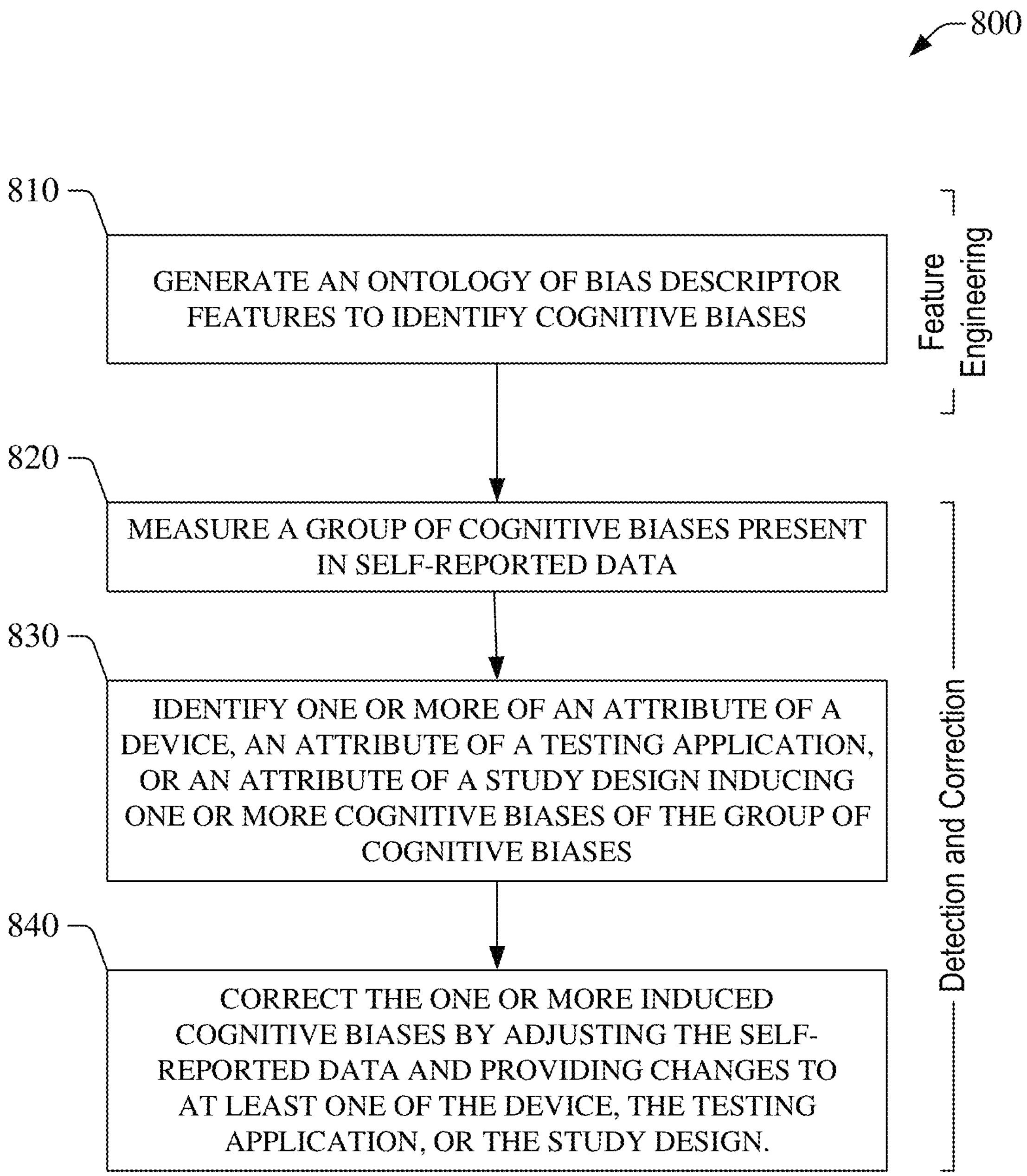
FIG. 8A illustrates a non-limiting example of a computer-implemented method for detecting and correcting cognitive bias in self-reported data, in accordance with one or more embodiments of this disclosure.

FIG. 8A illustrates a non-limiting example of a computer-implemented method 800 for detecting and correcting cognitive bias in self-reported data, in accordance with one or more embodiments of this disclosure. A computing system can implement, entirely or partially, the example method 800. Implementing the computer-implemented method 800 can include compiling or executing, or both, one or several of the blocks included in the computer-implemented method 800, for example. The computing system can include, and/or can be operatively coupled to, one or several processors, one or several memory devices, other types of computing resources (such as communication interface(s)), a combination thereof, or other similar resources. The computing system can embody, or can include, the bias assessment subsystem 130 (FIG. 1) and the bias correction subsystem 140 (FIG. 1).

At block 810, the computing system can generate an ontology of bias descriptor features (also referred to as β features) to identify cognitive biases. The cognitive biases can include a combination of at least one device-induced cognitive bias, at least one testing-application-induced cognitive bias, or at least one study-design-induced cognitive bias. In some embodiments, the computing system can execute one or more components (e.g., the generation subsystem 610 as is shown in FIG. 6B) to generate the ontology. Block 810 can embody a feature engineering stage and, in some embodiments, can include the blocks shown in FIG. 8B. Implementation of the feature engineering stage can provide a space of β features than can be used to assess cognitive biases.

At block 820, the computing system can measure a group of cognitive biases present in self-reported data (e.g., self-reported data 118 (FIG. 1). In some embodiments, the computing system can execute an evaluation component (e.g., evaluation component 320 (FIG. 3)) to measure the group of cognitive biases.

At block 830, the computing system can identify one or more of an attribute of a device (e.g., user device 110 (FIG. 1)), an attribute of a testing application, or an attribute of a study design inducing—collectively or individually—one or more cognitive biases of the group of cognitive biases. In some embodiments, the computing system can execute a characterization component (e.g., characterization component 330 (FIG. 3)) to identify such attributes.

At block 840, the computing system can correct the one or more induced genitive biases by adjusting the self-reported data and providing changes to at least one of the device, the testing application, or the study design. In some embodiments, the computing system can execute at least component (rectification component 520 (FIG. 5) and updated component 530 (FIG. 5), for example) to correct the cognitive bias(es) in such a fashion.

Blocks 820 to 840 can collectively embody a detection and correction stage. Implementation of that stage can permit removing the impact of β features on self-reported data.

Figure 8B:
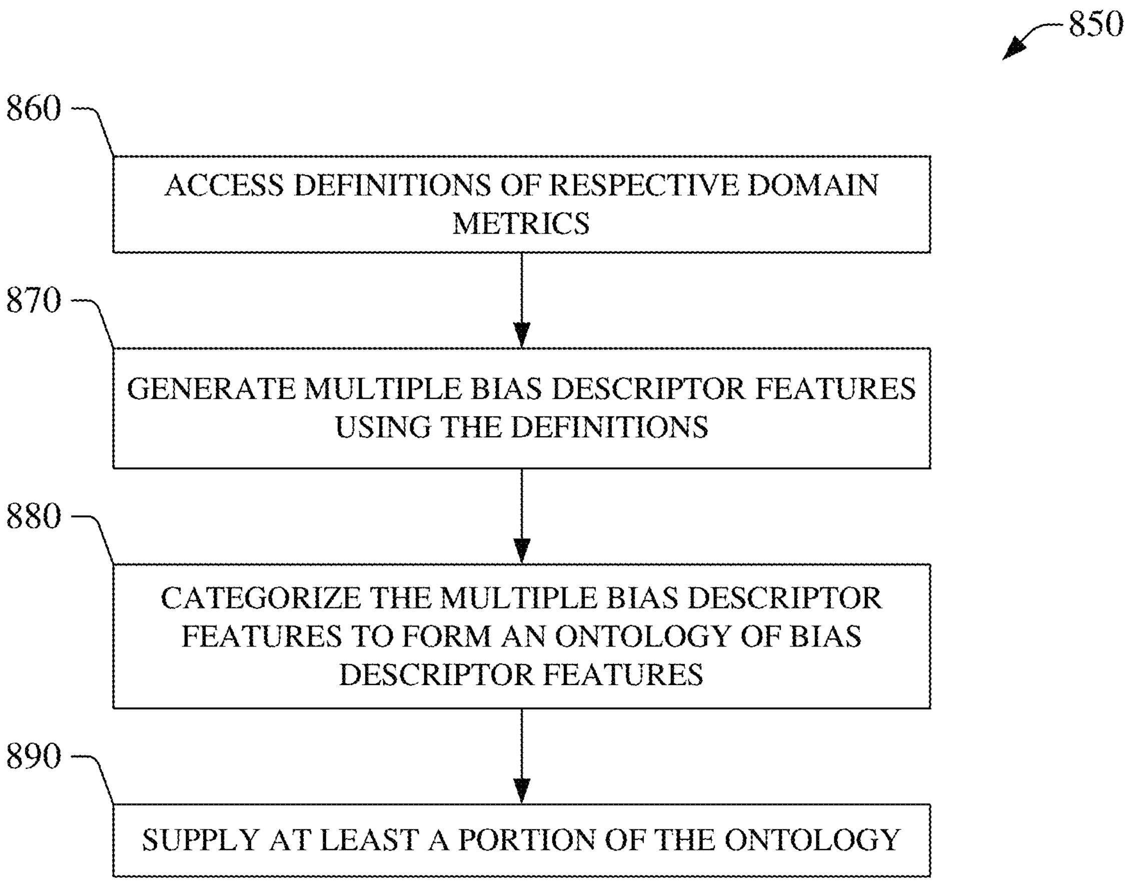
FIG. 8B illustrates a non-limiting example of a computer-implemented method for forming an ontology of β features, in accordance with one or more embodiments of this disclosure.

FIG. 8B illustrates a non-limiting example of a computer-implemented method 850 for forming an ontology of β features, in accordance with one or more embodiments of this disclosure. A computing system can implement, entirely or partially, the example method 850. Implementing the computer-implemented method 850 can include compiling or executing, or both, one or several of the blocks included in the computer-implemented method 850, for example. The computing system can include, and/or can be operatively coupled to, one or several processors, one or several memory devices, other types of computing resources (such as communication interface(s)), a combination thereof, or other similar resources. In some cases, the computing system can embody, or can include, the generation subsystem 610 (FIG. 6B, for example).

At block 860, the computing system can access definitions of respective domain metrics (e.g., domain metric definitions 616 (FIG. 6A). To that end, in some embodiments, the computing system can execute an ingestion component (e.g., ingestion component 630 (FIG. 6B). Such definitions can be included in a catalog of domain metrics (see Table 2, for example) and can be based on available raw data (e.g., device data or input data) for a study across multiple user devices (e.g., multiple user devices 108). As mentioned, a definition of a domain metric specifies a metric quantified by raw data obtained during the course of the study.

At block 870, the computing system can generate multiple bias descriptor features (β features) using the definitions. To that end, the computing system (via a feature composition component 64, for example) can apply a model to the definitions of domain metrics that have been accessed at block 860. The model (e.g., composition model 618 (FIG. 6A) can embodied in a machine-learning model or a genetic algorithm model that is trained to generate multiple bias descriptor features.

At block 880, the computing system can categorize (via the categorization component 650 (FIG. 6) for example) the multiple bias descriptor features to form an ontology of bias descriptor features. The formed ontology can be embodied in a collection of bias descriptor features organized in one or several categories.

At block 890, the computing system can supply at least a portion of the ontology. To that end, in some embodiments, the computing system can execute an output component (e.g., output component 660 (FIG. 6B)). Supplying at least the portion of the ontology can include sending at least a subset of the collection of bias descriptor features to a computing subsystem (e.g., bias assessment subsystem 130 (see FIG. 6A, for example). In some cases, the computing subsystem can be a part of the computing subsystem. In other cases, the computing subsystem can be remotely located relative to the computing system and operatively coupled thereto. In some embodiments, supplying at least the portion of the ontology can include generating a graphical representation of the portion of the ontology, and causing a display device to present the graphical representation. In some cases, the graphical representation can be edited using input data. An edited version of the graphical representation can cause the computing system to update the ontology of b features that is formed at block 880.

Figure 9:
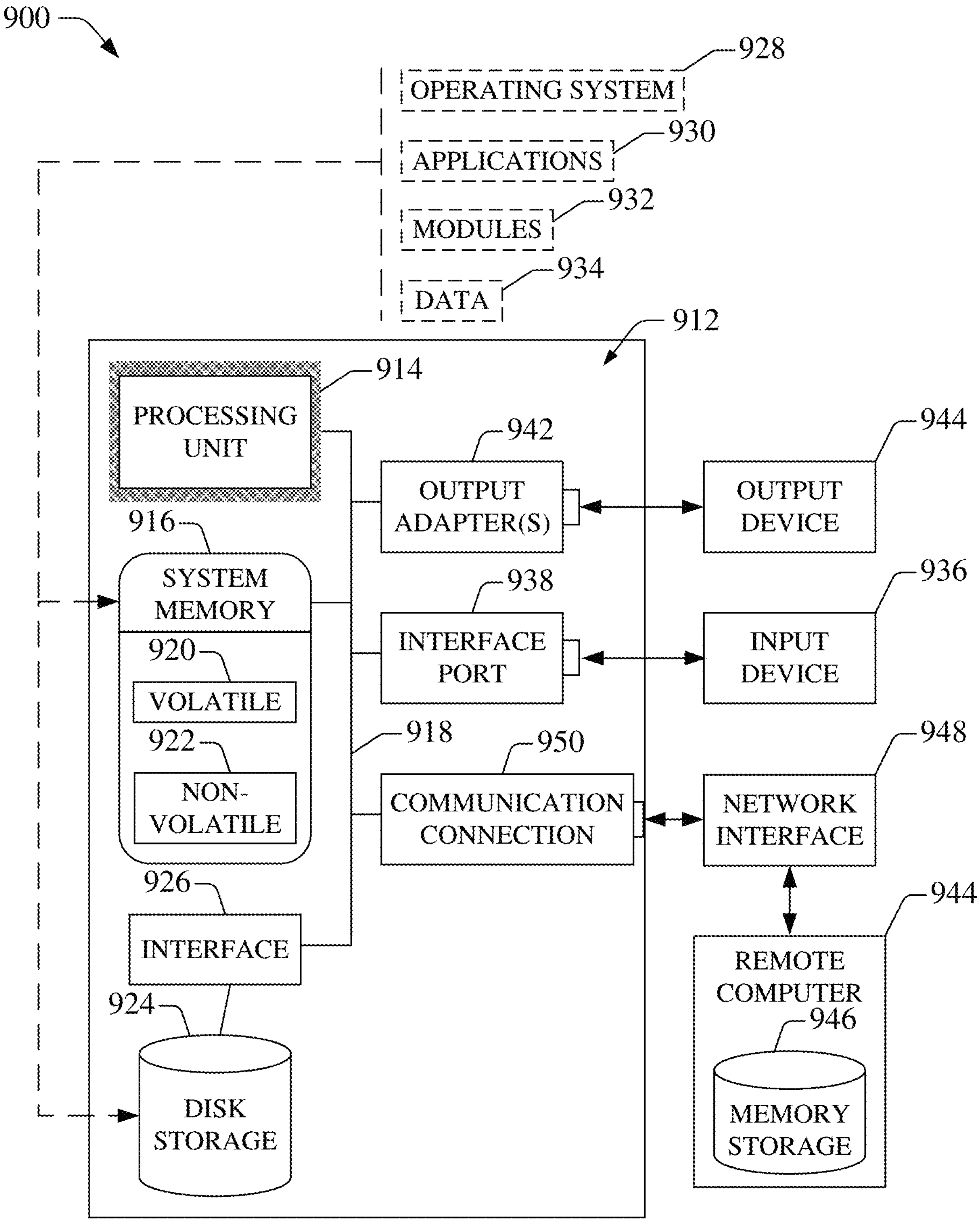
FIG. 9 is a block diagram of a non-limiting example of an operating environment in which one or more embodiments described herein can be implemented.

In order to provide a context for the various aspects of the disclosed subject matter, FIG. 9 as well as the following discussion are intended to provide a general description of a suitable environment in which the various aspects of the disclosed subject matter can be implemented. FIG. 9 illustrates a block diagram of an example, non-limiting operating environment in which one or more embodiments described herein can be facilitated. Repetitive description of like elements employed in other embodiments described herein is omitted for sake of brevity. A suitable operating environment 900 for implementing various aspects of this disclosure can include a computer 912. The computer 912 can also include a processing unit 914, a system memory 916, and a system bus 918. The system bus 918 can operably couple system components including, but not limited to, the system memory 916 to the processing unit 914. The processing unit 914 can be any of various available processors. Dual microprocessors and other multiprocessor architectures also can be employed as the processing unit 914. The system bus 918 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 916 can also include volatile memory 920 and nonvolatile memory 922. The basic input/output system (BIOS), containing the basic routines to transfer information between elements within the computer 912, such as during start-up, can be stored in nonvolatile memory 922. By way of illustration, and not limitation, nonvolatile memory 922 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 920 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 912 can also include removable/non-removable, volatile/non-volatile computer storage media. FIG. 9 illustrates, for example, a disk storage 924. Disk storage 924 can also include, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 924 to the system bus 918, a removable or non-removable interface can be used, such as interface 926. FIG. 9 also depicts software that can act as an intermediary between users and the basic computer resources described in the suitable operating environment 900. Such software can also include, for example, an operating system 928. Operating system 928, which can be stored on disk storage 924, acts to control and allocate resources of the computer 912. System applications 930 can take advantage of the management of resources by operating system 928 through program modules 932 and program data 934, e.g., stored either in system memory 916 or on disk storage 924. It is to be appreciated that this disclosure can be implemented with various operating systems or combinations of operating systems. A user enters commands or information into the computer 912 through one or more input devices 936. Input devices 936 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 914 through the system bus 918 via one or more interface ports 938. The one or more Interface ports 938 can include, for example, a serial port, a parallel port, a game port, and a universal serial bus (USB). One or more output devices 940 can use some of the same type of ports as input device 936. Thus, for example, a USB port can be used to provide input to computer 912, and to output information from computer 912 to an output device 940. Output adapter 942 can be provided to illustrate that there are some output devices 940 like monitors, speakers, and printers, among other output devices 940, which require special adapters. The output adapters 942 can include, by way of illustration and not limitation, video and sound cards that provide a means of connection between the output device 940 and the system bus 918. It should be noted that other devices and/or systems of devices provide both input and output capabilities such as one or more remote computers 944.

Computer 912 can operate in a networked environment using logical connections to one or more remote computers, such as remote computer 944. The remote computer 944 can be a computer, a server, a router, a network PC, a workstation, a microprocessor based appliance, a peer device or other common network node and the like, and typically can also include many or all of the elements described relative to computer 912. For purposes of brevity, only a memory storage device 946 is illustrated with remote computer 944. Remote computer 944 can be logically connected to computer 912 through a network interface 948 and then physically connected via communication connection 950. Further, operation can be distributed across multiple (local and remote) systems. Network interface 948 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 950 refers to the hardware/software employed to connect the network interface 948 to the system bus 918. While communication connection 950 is shown for illustrative clarity inside computer 912, it can also be external to computer 912. The hardware/software for connection to the network interface 948 can also include, for exemplary purposes only, internal and external technologies such as, modems including regular telephone grade modems, cable modems and DSL modems, ISDN adapters, and Ethernet cards.

In some embodiments, the control hub system 110 described herein can be associated with a cloud computing environment. For example, the bias assessment subsystem 130 and/or the bias correction subsystem 140 can be associated with a cloud computing environment 1050 included in the operational environment 1000 illustrated in FIG. 10, and/or with one or more functional abstraction layers described herein with reference to FIG. 11 (e.g., hardware and software layer 1160, virtualization layer 1170, management layer 1180, and/or workloads layer 1190).

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 10:
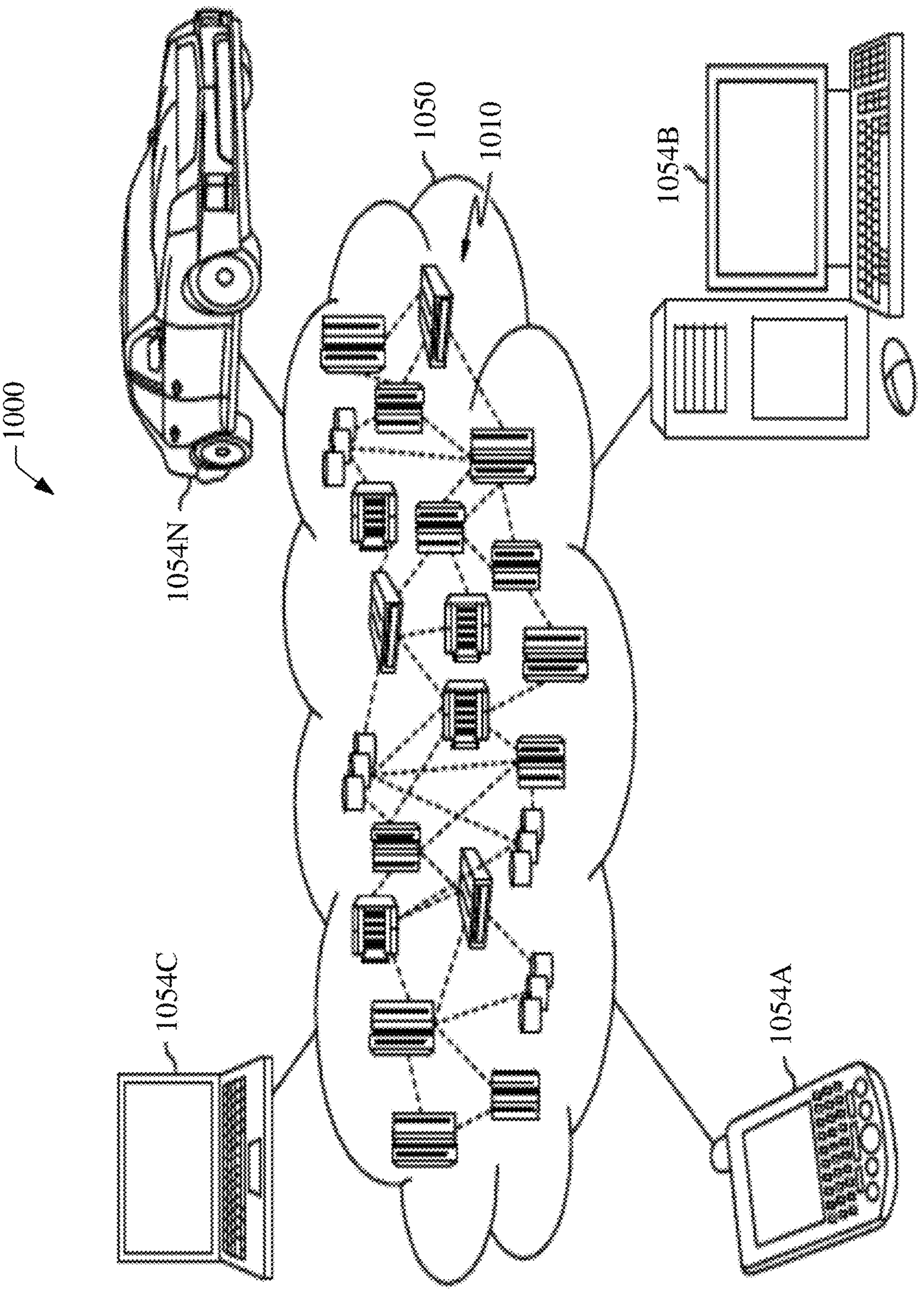
FIG. 10 is a block diagram of a non-limiting example of a cloud computing environment in accordance with one or more embodiments described herein.

Referring now to FIG. 10 an illustrative cloud computing environment 1050 is depicted. As shown, cloud computing environment 1050 includes one or more cloud computing nodes 1010 with which local computing devices used by cloud consumers, such as, for example, personal digital assistant (PDA) or cellular telephone 1054A, desktop computer 1054B, laptop computer 1054C, and/or automobile computer system 1054N may communicate. Although not illustrated in FIG. 10, cloud computing nodes 1010 can further comprise a quantum platform (e.g., quantum computer, quantum hardware, quantum software, and/or another quantum platform) with which local computing devices used by cloud consumers can communicate. Nodes 1010 may communicate with one another. They may be grouped (not shown) physically or virtually, in one or more networks, such as Private, Community, Public, or Hybrid clouds as described hereinabove, or a combination thereof. This allows cloud computing environment 1050 to offer infrastructure, platforms and/or software as services for which a cloud consumer does not need to maintain resources on a local computing device. It is understood that the types of computing devices 1054A-N shown in FIG. 10 are intended to be illustrative only and that computing nodes 1010 and cloud computing environment 1050 can communicate with any type of computerized device over any type of network and/or network addressable connection (e.g., using a web browser).

Figure 11:
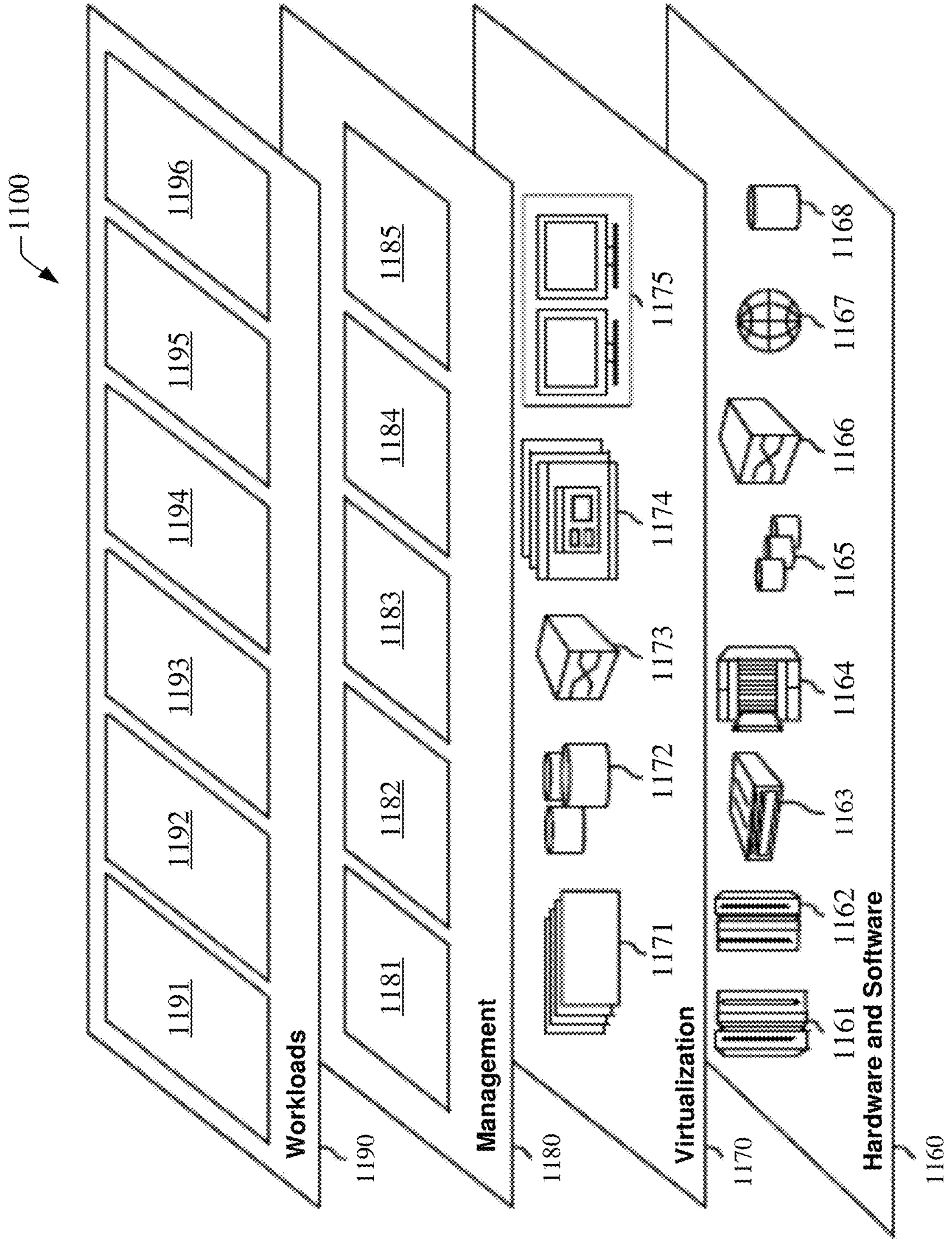
FIG. 11 is a block diagram of a non-limiting example of abstraction model layers in accordance with one or more embodiments described herein.

Referring now to FIG. 11, a set of functional abstraction layers provided by cloud computing environment 1050 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 1160 include hardware and software components. Examples of hardware components include: mainframes 1161; RISC (Reduced Instruction Set Computer) architecture based servers 1162; servers 1163; blade servers 1164; storage devices 1165; and networks and networking components 1166. In some embodiments, software components include network application server software 1167, database software 1168, quantum platform routing software (not illustrated in FIG. 11), and/or quantum software (not illustrated in FIG. 11).

Virtualization layer 1170 provides an abstraction layer from which the following examples of virtual entities may be provided: virtual servers 1171; virtual storage 1172; virtual networks 1173, including virtual private networks; virtual applications and operating systems 1174; and virtual clients 1175.

In one example, management layer 1180 may provide the functions described below. Resource provisioning 1181 provides dynamic procurement of computing resources and other resources that are utilized to perform tasks within the cloud computing environment. Metering and pricing 1182 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1183 provides access to the cloud computing environment for consumers and system administrators. Service level management 1184 provides cloud computing resource allocation and management such that required service levels are met. Service Level Agreement (SLA) planning and fulfillment 1185 provide pre-arrangement for, and procurement of, cloud computing resources for which a future requirement is anticipated in accordance with an SLA.

Workloads layer 1190 provides examples of functionality for which the cloud computing environment may be utilized. Non-limiting examples of workloads and functions which may be provided from this layer include: mapping and navigation 1191; software development and lifecycle management 1192; virtual classroom education delivery 1193; data analytics processing 1194; transaction processing 1195; and vulnerability risk assessment software 1196.

Embodiments of the present invention may be a system, a method, an apparatus and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "module," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units.

In this disclosure, terms such as "store," "storage," "data store," data storage," "database," "repository," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a memory configured to store computer-executable components; and a processor that executes at least one of the computer-executable components that:

measures, using at least one sensor of a wearable device worn by a user, at least one physiological state of the user;

generates, via a user interface of the wearable device, a prompt related to the at least one physiological state that requests the user to provide self-reported data;

receives, via the user interface, the self-reported data from the user;

creates, based on the at least one physiological state and the self-reported data, an ontology of bias descriptor features;

identifies, based on the ontology of bias descriptor features, cognitive biases comprising a combination of at least one device-induced cognitive bias, at least one testing-application-induced cognitive bias, or at least one study-design-induced cognitive bias; and adjusts the self-reported data to correct for the cognitive biases.

2. The system of claim 1, wherein a first one of the bias descriptor features represents at least one of an attribute of a device, an attribute of a testing application, or an attribute of study design affecting user state, and wherein a second one of the bias descriptor features represents at least one of a user behavior or a user experience in response to the study design.

3. The system of claim 2, wherein the at least one of the computer-executable components further:

measures a group of cognitive biases; and identifies one or more of a second attribute of the device, a second attribute of the testing application, or a second attribute of study design inducing one or more cognitive biases of the group of cognitive biases.

4. The system of claim 3, wherein measuring the group of cognitive biases comprises measuring, using a collection of predictive models, an impact of each one of the bias descriptor features in inducing the one or more cognitive biases.

5. The system of claim 3, wherein measuring the group of cognitive biases further comprises measuring, using a collection of predictive models, a collective impact of at least a subset of the bias descriptor features in inducing the one or more cognitive biases.

6. The system of claim 2, wherein the at least one of the computer-executable components further changes at least one of the device, the testing application, or the study design based on the adjustments to the self-reported data.

7. The system of claim 5, wherein adjusting the self-reported data comprises removing a particular cognitive bias of the one or more cognitive biases from the self-reported data.

8. The system of claim 2, wherein the at least one of the computer-executable components further causes, based on at least one bias descriptor feature, a change to at least one of the device, the testing application, or the study design.

9. A computer-implemented method, comprising:

measuring, by a system operatively coupled to a processor, using at least one sensor of a wearable device worn by a user, at least one physiological state of the user;

generating, by the system, via a user interface of the wearable device, a prompt related to the at least one physiological state that requests the user to provide self-reported data;

receiving, by the system, via the user interface, the self-reported data from the user;

generating, by the system, based on the at least one physiological state and the self-reported data, an ontology of bias descriptor features;

identifies, by the system, based on the ontology of bias descriptor features, cognitive biases comprising a combination of at least one device-induced cognitive bias, at least one testing-application-induced cognitive bias, or at least one study-design-induced cognitive bias; and adjusting, by the system, the self-reported data to correct for the cognitive biases.

10. The computer-implemented method of claim 9, wherein a first one of the bias descriptor features represents at least one of an attribute of a device, an attribute of a testing application, or an attribute of study design affecting user state, and wherein a second one of the bias descriptor features represents at least one of a user behavior or a user experience in response to the study design.

11. The computer-implemented method of claim 10, further comprising:

measuring, by the system, a group of cognitive biases; and identifying, by the system, one or more of a second attribute of the device, a second attribute of the testing application, or a second attribute of study design inducing one or more cognitive biases of the group of cognitive biases.

12. The computer-implemented method of claim 11, wherein the measuring comprises measuring, by the system, using a collection of predictive models, an impact of each one of the bias descriptor features in inducing the one or more cognitive biases.

13. The computer-implemented method of claim 11, wherein the measuring comprises measuring, by the system, using a collection of predictive models, a collective impact of at least a subset of the bias descriptor features in inducing the one or more cognitive biases.

14. The computer-implemented method of claim 10, further comprising changing, by the system, at least one of the device, the testing application, or the study design based on the adjustments to the self-reported data.

15. A computer program product for assessment of cognitive biases in self-reported data, the computer program product comprising a computer-readable storage medium having program instructions embodied therewith, the program instructions executable by a processor to cause the processor to:

measure, by the processor, using at least one sensor of a wearable device worn by a user, at least one physiological state of the user;

generate, by the processor, via a user interface of the wearable device, a prompt related to the at least one physiological state that requests the user to provide the self-reported data;

receive, by the processor, via the user interface, the self-reported data from the user;

generate, by the processor, based on the at least one physiological state and the self-reported data, an ontology of bias descriptor features;

identify, by the processor, based on the ontology of bias descriptor features, the cognitive biases comprising a combination of at least one device-induced cognitive bias, at least one testing-application-induced cognitive bias, or at least one study-design-induced cognitive bias; and adjust, by the processor, the self-reported data to correct for the cognitive biases.

16. The computer-program product of claim 15, wherein a first one of the bias descriptor features represents at least one of an attribute of a device, an attribute of a testing application, or an attribute of study design affecting user state, and wherein a second one of the bias descriptor features represents at least one of a user behavior or a user experience in response to the study design.

17. The computer-program product of claim 16, wherein the program instructions are further executable by the processor to cause the processor to:

measure a group of cognitive biases; and identify one or more of a second attribute of the device, a second attribute of the testing application, or a second attribute of study design inducing one or more cognitive biases of the group of cognitive biases.

18. The computer-program product of claim 17, wherein the program instructions are further executable by the processor to cause the processor to measure, using a collection of predictive models, an impact of each one of the bias descriptor features in inducing the one or more cognitive biases.

19. The computer-program product of claim 17, wherein the program instructions are further executable by the processor to cause the processor to measure, using a collection of predictive models, a collective impact of at least a subset of the bias descriptor features in inducing the one or more cognitive biases.

20. The computer-program product of claim 16, wherein the program instructions are further executable by the processor to cause the processor to change at least one of the device, the testing application, or the study design based on the adjustments to the self-reported data.

* * * * *